United States Patent [19]
Rose-Pehrsson et al.

[11] Patent Number: 5,469,369
[45] Date of Patent: Nov. 21, 1995

[54] SMART SENSOR SYSTEM AND METHOD USING A SURFACE ACOUSTIC WAVE VAPOR SENSOR ARRAY AND PATTERN RECOGNITION FOR SELECTIVE TRACE ORGANIC VAPOR DETECTION

[75] Inventors: Susan L. Rose-Pehrsson, Alexandria; Daniel Di Lella, Lorton, both of Va.; Jay W. Grate, West Richland, Wash.

[73] Assignee: The United States of America as represented by the Secretary of the Navy, Washington, D.C.

[21] Appl. No.: 970,750

[22] Filed: Nov. 2, 1992

[51] Int. Cl.⁶ .................................................. G01N 29/00
[52] U.S. Cl. .......................... 364/497; 364/496; 364/499; 340/632; 73/23.2
[58] Field of Search .................................. 364/496, 497, 364/498, 499; 340/632; 73/23.2

[56] References Cited

U.S. PATENT DOCUMENTS

| | | | |
|---|---|---|---|
| 4,055,072 | 10/1977 | Fletcher et al. | 73/23 |
| 4,312,228 | 1/1982 | Wohltjen | 73/597 |
| 4,638,443 | 1/1987 | Kaneyasu et al. | 364/497 |
| 4,661,913 | 4/1987 | Wu et al. | 364/500 |
| 4,869,874 | 9/1989 | Falat | 422/53 |
| 4,943,929 | 7/1990 | Simonoff | 364/496 |
| 4,979,124 | 12/1990 | Sachse et al. | 364/507 |
| 5,014,217 | 5/1991 | Savage | 364/498 |
| 5,120,421 | 6/1992 | Glass et al. | 204/406 |
| 5,121,338 | 6/1992 | Lodder | 364/498 |
| 5,412,465 | 5/1995 | Baylor et al. | 356/301 |

*Primary Examiner*—Ellis B. Ramirez
*Assistant Examiner*—Patrick J. Assovad
*Attorney, Agent, or Firm*—Thomas E. McDonnell; George A. Kap

[57] ABSTRACT

A method and a system using that method are provided which employ a pattern recognition algorithm to improve sensitivity in detecting hazardous vapors. The algorithm enables the discrimination of vapors of interest from non-hazardous substances at higher concentrations in varying relative humidity. A weight vector is generated corresponding to a N-space representation of a class comprising known vapors of interest, and a N-space representation of the unknown vapor is used to generate an unknown pattern vector. By calculating the dot product of the unknown pattern vector and the weight vector a determination can be made as to whether the unknown vapor is within the class. The weight vector is generated by selecting a training set comprising a subset of the known vapors of interest and background vapors and generating an N-space representation of the training set so as to create an associated weight vector.

12 Claims, 3 Drawing Sheets

SMART SENSOR SYSTEM AND METHOD USING A SURFACE ACOUSTIC WAVE VAPOR SENSOR ARRAY AND PATTERN RECOGNITION FOR SELECTIVE TRACE ORGANIC VAPOR DETECTION

FIELD OF THE INVENTION

This invention relates generally to systems for sensing or detecting the presence of various vapors and, more specifically, to an improved system and method for the detection of chemical warfare agents and other vapors.

BACKGROUND OF THE INVENTION

The detection of chemical warfare agents in field environments represents a very challenging analytical problem. These toxic agents must be detected at trace concentrations under conditions where other background vapors may be present at much higher concentrations. Therefore, detectors for this purpose must be extremely sensitive, yet highly selective at the same time. Such detectors must provide reliable reports of hazards without generating false alarms.

During the 1980's small chemical sensors based on microelectronic devices emerged as the leading technology for a variety of chemical detection problems. A number of these sensor technologies have been developed and investigated, including optical waveguide chemical sensors, chemiresistors, and surface acoustic wave (SAW) vapor sensors.

For example, U.S. Pat. No. 4,869,874 (Falat) discloses an environmental monitoring apparatus which includes sensors which measure pressure, temperature, relative humidity, and the corrosive nature of the environment. The signals generated by the sensors are stored in a memory module wich may interface with a convention personal computer.

U.S. Pat. No. 4,661,913 discloses an optical comparator and classifier device which operates by having training objects which moved substantially one at a time, in a fluid flow stream. An incident beam of illumination is provided so as to be directed at the training objects in the flow stream. Data associated with each moving training object as the object passes through the beam of illumination is collected. A class of objects is established from this data, these objects having common characteristics based on the data detected from such class of objects. The data is then stored. This stored data is compared to data detected from sample objects of an unknown class. A determination is then made that the objects from the unknown class belong to the established class as a result of directly matching the respective data.

U.S. Pat. No. 5,014,217 (Savage) discloses an apparatus and method for automatically identifying the chemical species within a plasma reactor environment. The apparatus and method include a means for measuring an optical emission spectrum of the chemical species in the plasma and a library containing a multiplicity of predefined spectral patterns. A processor automatically correlates the spectrum with the predefined spectral patterns in the library and yields a correlation value for all the correlations. A subset of the predefined spectral patterns based upon the highest correlation values are selected and used to identify the chemical species and abundances thereof in the plasma.

U.S. Pat. No. 5,120,421 (Glass et al.) discloses an electrochemical sensor which utlizes a multielement, microelectrode array detector for gathering a plurality of signals which form a profile. This profile is then compared to a library of profile responses to determine which library profile best matches the current profile. By determining the closest profile, the compound may be identified.

Both the SAW and chemiresistor chemical microsensors are capable of detecting chemical warfare (CW) agents with high sensitivity. The selectivity provided is substantial but can be improved dramatically through the use of arrays of sensors whose responses are analyzed using pattern recognition algorithms. The above patents disclose the use of a rudimentary pattern recogniton algorithm, i.e. direct correlation to a test set.

SAW sensors are readily adapted to sensor array systems because of the great flexibility in tailoring the chemical selectivity of the individual sensors, and the in depth understanding of their response mechanisms. As a result, SAW vapor sensors have become the leading microsensor technology for chemical warfare agent detection.

The development and testing of sensor systems is an interdisciplinary effort that requires a variety of expertises. These areas include microsensor devices, vapor chemical and physical properties, chemically selective coating materials, microsensor arrays and pattern recognition, sensor system design and integration, automated sensor testing, and finally sensitivity and selectivity concepts.

Other patents of interest in the area of detection systems include U.S. Pat. No. 4,979,124 (Sachse et al.) which discloses a method and system which utilizes an adaptive neural-based signal processor for analyzing emission signals emenating from a test medium for the purpose of determining characteristics of the test medium. In addition, U.S. Pat. No. 5,121,338 (Lodder) discloses a method for using spectral analysis to detect subpopulations. According to this method, a training set of spectra of a first plurality of samples is obtained and a bootstrap distribution is formed therefrom. A test set of spectra from a second plurality of samples is then obtained and a second bootstrap distribution is formed therefrom. First and second univariate distributions are then formed from the respective bootstrap distributions. A quantile-quantile relationship of the training sets is then developed and a determination of whether the test set and the traning set are substantially identical is made from this relationship.

SUMMARY OF THE INVENTION

According to the invention, a method and system are provided which enables vapors of interest, such as chemical warfare agents, to be discriminated from other vapors or substances, i.e., non-hazardous substances, at higher concentration in varying relative humidity.

In accordance with a first aspect the invention, a method is provided for identifying an unknown vapor as either belonging to a class or not, wherein the class comprises known vapors of interest, the method comprising the steps of generating a weight vector corresponding to a N-space representation of the class; generating a N-space representation of the unknown vapor and generating an unknown pattern vector based thereon; and calculating the dot product of said unknown pattern vector and the weight vector to determine whether the unknown vapor is within said class.

Preferably the step of generating a weight vector comprises the steps of: selecting a training set comprising a subset of the known vapors of interest and background vapors; generating an N-space representation of said training set so as to create an associated weight vector; and storing said weight vector in memory for use when the dot product is calculated.

Advantageously, the step of generating an N-space representation of said training set further comprises the steps of: generating vapor response data from a sensor array comprising at least two sensors; plotting a pattern of responses as points in an N-dimensional feature space having N axes and defining a pattern vector extending from the origin of said axes to said point, where N is defined by the number of sensors in said sensor array; and using a supervised learning technique to generate a discriminant function which defines a weight vector, a first cluster of points corresponding to the known vapors, and a second cluster of points corresponding to the background vapors.

In one preferred embodiment, the step of using supervised learning techniques to generate a discriminant function further comprises the step of: using a parametric equation to iteratively generate said weight vector.

In one implementation of this embodiment, using the parametric equation involves using a Bayes decision function. Preferably, the vapor response data from said sensor array is multiplied by a constant.

Advantageously, the dot product is compared with a vector associated with each known pattern result to determine if a correction factor is required, and this step is iteratively repeated until all results agree with known results.

In accordance with another embodiment, the step of using a supervised learning technique to generate a discriminant further comprises using a nonparametric equation to iteratively generate said weight vector. Using this nonparametric equation preferably comprises using a linear learning machine.

The step of using a supervised learning technique to generate a discriminant preferably further comprises the step of: using a parametric equation to iteratively generate said weight vector; and passing said weight vector to at least one further supervised learning technique to increase the accuracy of the weighing vector.

The step of generating a N-space representation of the unknown vapor preferably comprises the steps of: generating unknown vapor response data from a sensor array comprising at least two sensors; and plotting a pattern of said unknown response as a point in an N-dimensional feature space having N axes and defining an unknown pattern vector extending from the origin of said axes to said point, where N is defined by the number of sensors in the sensor array.

In accordance with a further aspect of the invention, a smart sensor system is provided for determining whether an unknown vapor is within a known class of vapors, the system comprising: a sampling means for generating vapor samples; an array of N sensors for generating vapor response data from said vapor samples; means for plotting said response data as points in an N-dimensional feature space having N axes and defining unknown pattern vectors, each vector being associated with one of said points and extending from the origin of said axes to said point; and means for calculating the dot product of said unknown pattern vector and a stored weight vector associated with a N-space representation of the known class to determine if said vapor is within said class.

Preferably, each of said sensors comprises a transducer having vapor sensitive coating disposed thereon for providing sorbing of said vapors to thereby increase the mass and decrease the modulus of said coating. The vapor sensitive coating can be selected from the group consisting of poly(ethylenimine), fluoropolyol, ethyl cellulose, poly(epichlorohydrin), poly(isobutylene), poly(ethylene maleate), poly(ethylene phthalate), and combinations thereof. A temperature control circuit is advantageously provided for maintaining said sensors at a predetermined temperature.

Other features and advantages of the invention will be set forth in, or apparent from, the following detailed description of the preferred embodiment of the invention.

DESCRIPTION OF THE PREFERRED EMBODIMENTS

Figure 1:
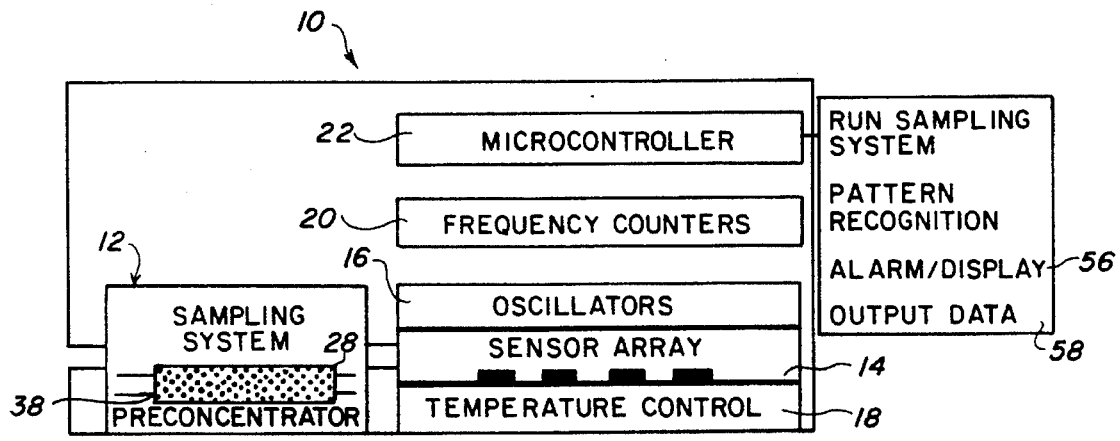
FIG. 1 is a block diagram of a smart sensor system constructed in accordance with a preferred embodiment of the invention.

Referring now to the drawings, FIG. 1 illustrates a preferred embodiment of the invention in which a smart sensor system, generally denoted 10, is illustrated. As illustrated, the smart sensor system 10 comprises a sampling system 12, an array of sensors 14 which are operated in corresponding oscillator circuits 16, a temperature control system 18, frequency counters 20, and at least one microcontroller 22. Each of the above identified elements is discussed in greater detail below.

Sampling System

Figure 2:
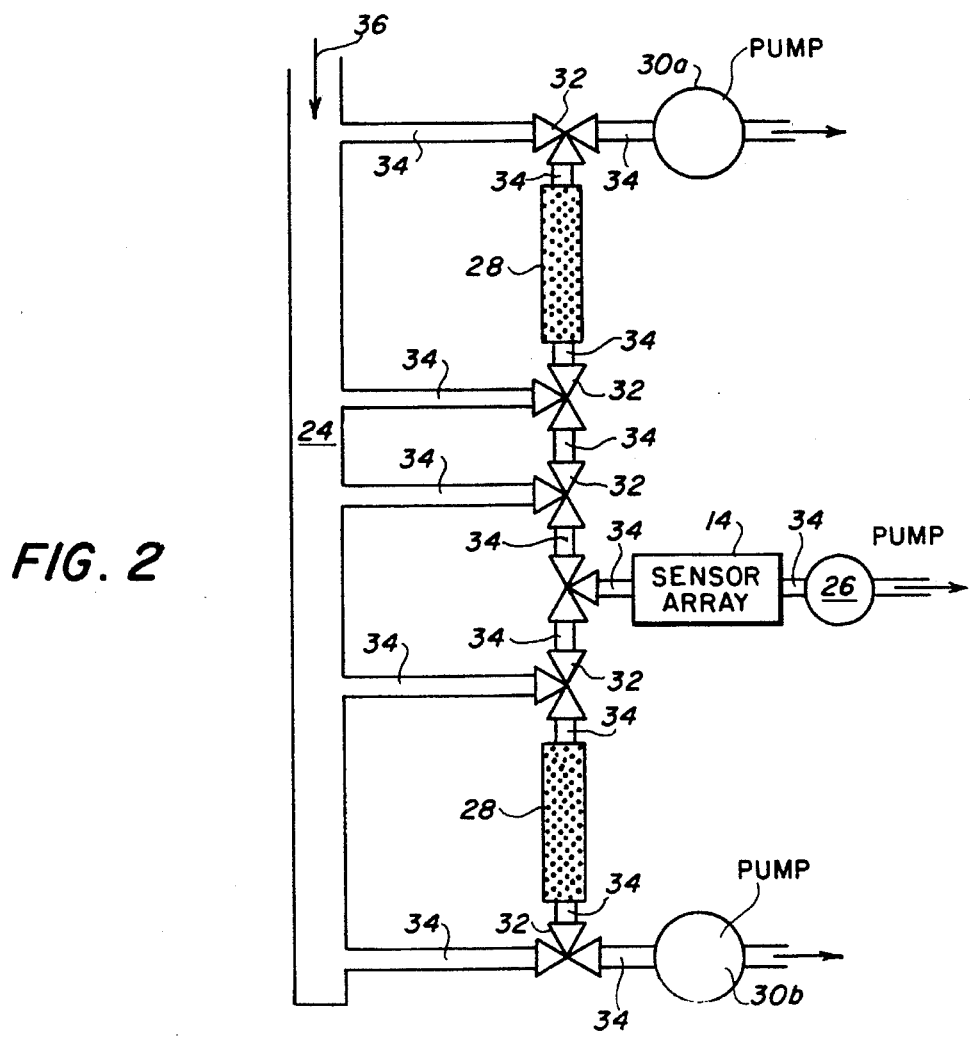
FIG. 2 is a fluid circuit diagram of a sampling system utilized in the smart sensor system of FIG. 1.

Turning to FIG. 2, the sampling system 12 consists of a sampling manifold 24, a small pump 26 to pull samples through the sensor array 14, two preconcentrator tubes 28, two large pumps 30a and 30b (one associated with each preconcentrator tube), and a plurality of solenoid valves 32, connected as shown. The sampling system 12 is constructed with Teflon wetted parts and a connecting tubing 34 is provided between the above identified components or unit which, in a preferred embodiment, is 1/8 inch OD 1/16 inch ID throughout, except as noted below.

The sampling manifold 24 allows sample air to be drawn into the sampling system 12 as indicated by directional arrow 36. In the field, the sample air would be identical to the ambient air in the environment being sampled. In the laboratory, sample air is the calibrated gas stream that is delivered to the sampling manifold 24. This gas stream consists of carrier gas at a fixed humidity which can be delivered with or without the test vapor. In laboratory testing, sample air is not the same as the ambient laboratory atmosphere.

The preconcentrator tubes 28 are included because they enhance both sensitivity and selectivity of the sensors in sensor array 14. These tubes 28 and devices which collect vapors by sorption into a tube of solid polymeric sorbent. The tubes 28 are heated periodically to desorb the vapors for detection by the sensors. This method is employed to increase the sensitivity of the sensor system. It was found, however, that the use of this method also increased the selectivity of the systems by virtue of the differences in collection efficiencies and desorption times among various vapors.

The preconcentrator tubes 28 each consist of a ¼ inch OD ⅛ inch ID glass tube (not shown) packed with 40–60 mesh Tenax over approximately a ¼ inch length of the tube. The Tenax is held in place with glass wool, and ⅛ inch OD Teflon tubing is press fit into the ends of the glass tube up to the glass wool. A sleeve of Tygon tubing over (not shown) the junction where the Teflon tube enters the glass tube prevents leaks. A coil of nichrome wire (not shown) wrapped around the glass tube is used to thermally desorb sample from the Tenax. The wire coil and a thermocouple (not shown) are held to the tube with a high temperature adhesive. A control circuit (not shown) heats the tube to approximately 200° C. during the thermal desorption. The two tubes in the system are identical in construction but are operated on different timing cycles.

A sample is collected on the Tenax of a tube 28 by pulling sample air through the Tenax with a large pump 30 at ca. 800 mL/min. At the programmed time, the valves 32 are switched so that sample air functioning as carrier gas is pulled through the Tenax of the tube 28 in the opposite direction and over the sensor array 14 by the small pump 26 pulling at ca. 75 mL/min. Then the Tenax of tube 28 is heated and the sample is thermally desorbed. Thus preconcentration is achieved in two dimensions, time and flow rate.

Three sampling modes are used in this instrument. In direct mode, the sensors in array 14 are exposed to sample air directly. The term direct as used here means that the gas flowing over the sensor array 14 has not been passed through a preconcentrator tube 28. It has been drawn into the system 12, through the sampling manifold 24, through one or more valves 32, and into the sensor array 14. In two-minute preconcentrator mode, the sensors in array 14 are exposed to vapor desorbed from one of the preconcentrator tubes 28 operated on a two minute cycle. In fourteen-minute preconcentrator mode, the sensors of array 14 are exposed to vapor desorbed from the other preconcentrator tube 28 which is operated on a fourteen-minute cycle.

The total sensor system 10 can be started up and operated in two ways. These are referred to as operating modes, and should not be confused with the three sampling modes. With the preconcentrators 28 off (preconcentrators-off operational mode), the only sampling mode is the direct mode. With the preconcentrators 28 on (preconcentrators-on operational mode), the sampling system 12 delivers samples in all three types of sampling modes to the sensors of array 14 on a pre-programmed schedule. The latter is the normal operating condition of the system 10, and it will be described in great detail below.

In normal preconcentrators-on operational mode, one of the preconcentrator tubes 28 is operated on a two-minute cycle and the other preconcentrator tube 28 operated on a fourteen-minute cycle. Combined with direct sampling of the atmosphere without preconcentration, these procedures resulted in three separate sampling modes: direct sampling mode, two-minute preconcentrator sampling mode, and fourteen-minute preconcentrator sampling mode.

The smart sensor system 10 may also be operated for test purposes in a preconcentrators-off mode where direct sampling is continuous and the preconcentrators are not used.

In normal preconcentrators-on operational mode, the two-minute preconcentrator 28 collects sample for 70 seconds. During this time the sensors of array 14 are in direct sampling mode, i.e., they are seeing sample air that is drawn into the system and delivered directly to the sensors without passing through a preconcentrator tube 28. Then the valves 32 are switched so that the sensors see air that is routed through the two-minute preconcentrator tube 28, and the large pump 30 associated with the two-minute preconcentrator 28 is turned off. A slight perturbation in sensor baselines may occur on valve switching. After 10 seconds for baseline stabilization, thermal desorption is begun and continues for 40 seconds. Then heating stops, the valves 32 are switched back so that the sensors of array 14 again see sample air directly, and the large pump is turned back on so that the Tenax again collects sample. The two-minute preconcentrator tube 28 is rapidly cooled because it is located near a fan.

The fourteen-minute preconcentrator 28 is operated similarly, except that it collects sample for 13 minutes and 10 seconds, followed by 10 seconds for baseline stabilization after valve 32 switching, and 40 seconds for thermal desorption.

During normal operation, the instruments operate on a pre-programmed schedule of sampling modes that repeats every fourteen minutes. This schedule was constructed by defining seven two minute cycles which comprise a fourteen-minute sampling period. During each two-minute cycle the sampling system 12 delivers sample air directly to the sensors of array 14 for a total for 70 seconds. For the other 50 seconds one of the preconcentrator tubes 28 is desorbed as described above. During each of the first six two-minute cycles (in the fourteen-minute sampling period) the two-minute preconcentrator tube 28a is desorbed. During the seventh two-minute cycle the fourteen-minute preconcentrator tube 28b is desorbed.

In normal operation the fourteen-minute sampling period schedule is repeated indefinitely, so the definition of the beginning of a period with the beginning of a two-minute preconcentrator cycle coincides with the beginning of sample collection on the two-minute preconcentrator tube 28. In viewing individual sensor response data presented graphically, it is convenient and logical to think of the cycles in that manner.

Figure 3:
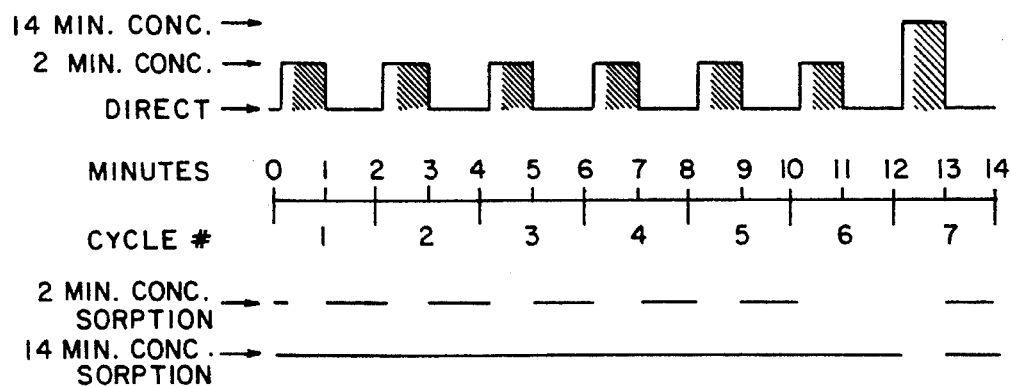
FIG. 3 is a timeline for one sampling period of the sampling system of FIG. 2.

For data collection purposes and analysis, however, cycles were defined as follows. For 10 seconds the sensors of array 14 see sample air directly. Then array 14 is exposed to a sample from a preconcentrator tube 28 for 50 seconds. This is followed by 60 seconds of direct sampling. The next cycle begins with 10 more seconds of direct sampling, and so on. A schematic time line of all seven cycles in one sampling period is shown in FIG. 3.

Finally, it is noted that the system 10 reports data to a serial port of microcontroller 22 every two seconds. Therefore, each two-minute cycle reports 60 data points. Frequency data are identified by their point number (1–60) in a particular cycle (1–7). Since it is convenient to refer to a data point by this numbering system, it is worthwhile to remember that when a time in a cycle is specified by its point number, the actual time elapsed since the beginning of the cycle in seconds is 2 times that number.

Two aspects of the sampling system that require attention are flow restrictions and the effects of leaks. In direct sampling mode there are three pumps, the two large pumps 30a and 30b and the small pump 26, pulling samples from the sampling manifold 24. These three pumps compete for the air in the manifold 24 if there is any restriction on the flow of air into the manifold 24. In the worst case, the two large pumps 30a and 30b can overwhelm the small pump 26 and the manifold 24 will pull air backwards through the small pump 26 and the sensor array 14.

Flow restrictions can arise if the bore of the manifold 24 is inadequate or if the tubing 34 connecting the manifold 24 to the system inlet 38 (see FIG. 1) is too narrow. It was found that ¼ inch OD ⅛ inch ID tubing connecting the manifold 24 to the system inlet 38 was sufficient, but that ⅛ inch OD 1/16 inch ID tubing was too narrow and caused a flow restriction. The tubing from the manifold 24 to the valves 32 is ⅛ inch OD 1/16 inch ID.

It is important to understand these effects if one considers placing a filter (not shown) for particulates on the system inlet 38. The filter must be designed so that it does not create a significant flow restriction.

The normal flow rates when there are no flow restrictions to the sampling manifold 24 are as follows. During direct sampling with all three pumps pulling on the manifold 24, the flow rate is ca. 100 mL/min across the sensor array.

When the sampling system 12 is switched to the two-minute preconcentrator 28, the flow rate drops to ca. 75 mL/min. Note that in this configuration only two pumps, pump 30b and pump 26, are pulling against the manifold. The flow rate drops because the air to the sensor array 14 must be pulled through the packed preconcentrator tube 28. A presure drop develops across this tube 28, and the pressure over the sensors of array 14 necessarily drops slightly relative to what it was during direct sampling. When the preconcentrator tube 28 is heated to thermally desorb the sample, the flow rate drops to ca. 50 mL/min. because the Tenax in the tube expands and and increases the pressure drop across the tube. The pressure over the sensors of array 14 must decrease at the same time.

When the sampling system is switched to the fourteen-minute preconcentrator 28 from direct sampling, the flow rate again drops from ca. 100 to ca. 75 mL/min. Note that in this configuration only the small pump 26 is pulling against the manifold 24. And on heating, the flow rate drops to ca. 50 mL/min., just as noted above for the other preconcentrator 28a.

Because the pressure over the sensors of array 14 changes as the system 10 is switched from one sampling mode to another, the effect of leaks on the sensors of array 14 can be dramatic. The PEI sensor (described below), which is particularly sensitive to humidity, was diagnostic for leaks. Consider the possibility of a leak in the lid of the sensor package. It will be assumed for the sake of this illustration that the vapor generation system is delivering a humidity that is different from that of the ambient air in the room. If there is no leak, the humidity in the sensor package will be the humidity delivered to the system inlet 38 by the vapor generation system modified by the humidity of the ambient air which is leaking into the package. The leak rate will depend on the size of the leakage pathway and the difference in pressure between the ambient air and the air in the package. When the valves 32 are switched from direct sampling mode to a preconcentrator mode, the pressure inside the sensor package drops slightly, the leak rate increases, and the humidity in the package changes. The PEI sensor responds to this change in humidity with a sudden change in frequency. This appears as an abrupt change in baseline on valve 32 switching. The other sensors may also show such changes to the extent that they are sensitive to humidity changes.

There are three diagnostics for the presence of these types of leaks. First, there is an apparent sudden change in baselines as the valves switch from one sampling mode to another. Second, the sensor which is most sensitive to humidity changes displays the largest baseline shift. Third, the direction of these baseline shifts will depend on whether the sample air at the system inlet is higher or lower in humidity than the ambient room air. When the room ambient air has higher humidity than the sample air, then switching from direct sampling mode to preconcentrator sampling mode (and increasing the leak rate) will increase the humidity in the sensor package and the sensors will respond accordingly. Note that when the humidity of the sample air and the ambient air are the same, as would be the case in field use, these effects are not seen.

A fourth method used to diagnose the presence of leaks is to place a helium leak detector (not shown) on the outlet of the small pump 26. Then a very low flow rate of helium from a pipette tip is directed at various portions of the system. If a leak is present where the pipette tip is directed, the system draws in the helium and delivers it to the helium leak detector, which responds. This method is tedious given the many parts and connections in the sampling system, and the necessity to make observations in all sampling modes, but a rigorously leak-free system is required.

Sensor Array

Figure 4:
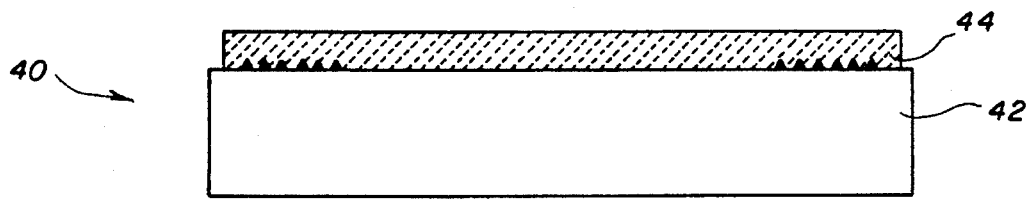
FIG. 4 is a schematic side elevational view of a surface acoustic wave sensor utilized in the smart sensor system of FIG. 1.

Turning now to FIG. 4, a chemical microsensor, generally denoted 40, is illustrated. The fabrication of a chemical microsensor 40 begins with an interdigital transducer 42, such as an acoustic device, a chemiresistor, or an optical waveguide. An example of an acoustic device, the preferred embodiment, is a surface acoustic wave (SAW) transducer or sensor. Of the commercially available SAW sensors, SAW sensors having SAW delay lines in frequencies of 31, 52, 112, 158, and 300 MHz are of particular interest in chemical warfare (CW) agent detection. SAW transducers convert an applied rf voltage into a Rayleigh surface wave when placed in an oscillator curcuit 16. In an alternative embodiment, chemiresistor sensors for hydrazine and organophosphorous detection may be utilized as microsensor 40. Optionally, a 5 MHz flexural plate wave device may also be utilized as microsensor 40.

Disposed over or applied to the surface of transducer 42 is a thin film 44 of a chemically selective material. The purpose of the thin film 44 is to collect and concentrate analyte molecules from the gas phase onto the surface of transducer 42. This process is called sorption. Sorption increases the mass and decreases the modulous of the thin film 44, both effects perturb the Rayleigh wave created by the transducer 42. The intradigital transducer 42 senses a change in the physical properties of the thin film 44 when the vapor is sorbed. This change or pertubation in the Rayleigh wave is detected electronically as a shift in the frequency of the oscillator circuits 16. SAW devices are capable of detecting minute changes in mass on their surfaces by this method. For a more detailed discussion on this subject, see H. Wohltjen "Mechanism of operation and design considerations for surface acoustic wave device vapor sensors," *Sens. Actuators* 5, 307–325, 1984.

The smart sensor system 10 utilizes individual chemical microsensors 40 as components. The apparent sensitivity and selectivity of the sensors 40 in the system 10 are highly dependent on the system design and the integration of all the parts that make up the system 10. In a preferred embodiment, an array 14 of SAW sensors is used wherein each sensor 10 has a different chemically selective coating or thin film 14. The individual sensor responses are evaluated with a pattern recognition algorithm (described below) to determine the system response, i.e., whether or not a CW hazard is present. The system 10 provides an appropriate environment for the sensors 40 and it delivers samples to them by the above described sampling system 12.

Sensitivity is defined as the incremental change in signal in response to an incremental change in analyte concentration. The sensitivity of an individual chemical microsensor 40 is determined by the amount of the selective thin film 44 on the surface of transducer 42, the strength with which the film 44 sorbs vapors, and the inherent sensitivity of the transducer 42 to changes in thin film 44 physical properties. The sensitivity of the overall sensor system can be made to be greater than that of any single sensor by using the preconcentration methods described above.

Detection limits are determined by the sensitivity and the signal noise. Individual chemical microsensors 40 can detect nerve agents, in the laboratory, to concentrations in the range of 0.1 to 0.5 $mg/m^3$. Detection limits of sensor systems 10 using preconcentrators 28 as described above can be reduced to levels of 0.01 $mg/m^3$ or less. The actual detection limits of interest, however, are the detection limits at which the system 10 provides reliable alarms. This requires selectivity in the system response.

Selectivity is determined by various components in the smart sensor system 10. The individual sensors 40 each have selectivities determined by the particular thin film 44 on their surfaces. Selectivities for nerve agents over potential background vapors such as water or hydrocarbon fuels can be 3 to 4 orders of magnitude. System selectivity is dramatically improved through the use of an array 14 of sensors in combination with pattern recognition, described below. In addition, the preconcentrator tubes 28 are not efficient at collecting water vapor or volatile organics, but are very efficient at collecting CW agent hazards. When the collected sample is thermally desorbed from the preconcentrator tube 28, further selectivity is achieved because the agents take longer to desorb than water or volatile organics. Thus, vapors are separated in time.

A variety of criteria are used to determine the number of sensors 40 in a sensor array 14 and the selection of the chemically selective coating materials 44 to be applied to the surfaces of the transducers 42. In the preferred embodiment, the sensor array 14 was limited to no more than four sensors because existing electronic hardware to collect and process sensor signals was designed for four sensors. It should be appreciated that any number of sensors 40 may be utilized in the array 14. The prototypes were designed to detect both nerve and blister CW agents, mandating that coatings be selected for both these detection applications and be placed in the same sensor array 14. This requirement determines the selection of at least two of the four sensor coatings.

The remaining coatings had to be selected to provide additional chemical information about the environment to aid in distinguishing between the agent hazards to be detected (target analytes) and background vapors to be ignored.

The selection of fluoropolyol as the nerve agent sensitive coating was made because of the extensive experience with this and other polymers which are good sorbents for nerve agents. For blister agents, it was decided that ethyl cellulose would be included in the array, and possibly also poly(epichlorohydrin). Including both would help to "hedge the bets" since there is no previous experience in classifying blister agents with a sensor array 14. However, sensors 40 with these two coatings were somewhat correlated (i.e., tended to respond similarly to a variety of vapors) in a study of nerve agent simulant classification, which could be disadvantageous since the correlation indicates that the two sensors do not provide significantly different chemical information to the pattern recognition algorithm, discused below, as two uncorrelated sensors would.

This approach left one or at most two additional coating materials to choose. Poly(ethylenimine) was selected primarily because it provides information about changes in humidity. In addition, it has distinctly different chemical characteristics from the other coating materials. Poly(ethylenimine) is a strong hydrogen bond base. Fluoropolyol is a strong hydrogen bond acid. Poly(epichlorohydrin) is only moderately basic and it is somewhat dipolar and polarizable. Similarly, ethyl cellulose is moderately basic and can also interact by dipolar interactions.

Ethyl cellulose differs from the other coatings in its physical characteristics. It is a glassy and crystalline polymer at the operating temperature of system 10. The other three are all non-crystalline materials above their glass transition temperatures at the system 10 operating temperature.

The possibility of including poly(isobutylene) in the array instead of poly(epichlorohydrin) was considered. Poly(isobutylene) interacts only by dispersion interactions and is most useful for providing information about hydrocarbons (e.g., in fuel vapors). It would be dissimilar to the other coatings in the array and might provide additional information that would be useful in the correct classification of vapors. However, it is not very sensitive to most vapors and therefore might not provide very much useful information. However, poly(epichlorohydrin) can also provide information about the presence of hydrocarbons, although it is less selective in this regard.

The possibility of including poly(ethylene maleate) or poly(ethylene phthalate) in the array instead of poly(epichlorohydrin) was also considered. Neither of these two polyesters is as closely correlated to ethyl cellulose as poly(epichlorohydrin). To investigate these possibilities, applicant considered three four sensor arrays, each containing fluoropolyol, ethyl cellulose, and poly(ethylenimine). The fourth coating was one of the three above. Then an investigation was conducted to determine the classification of nerve agent simulants by these three arrays using previously gathered data. The polyester-containing arrays were no more effective than that containing poly(epichlorohydrin).

It was ultimately decided to include poly(epichlorohydrin) as the fourth sensor coating in the array. The four coatings chosen are then fluoropolyol, poly(ethylenimine), ethyl cellulose, and poly(epichlorohydrin); these are sometimes referred to with the abbreviations FPOL, PEI, ECEL, and PECH, respectively. They were applied to the sensors 40 in films 44 whose mass per unit areas caused ca. 250 kHz of frequency shift in the sensor signal. This corresponds to ca. 40 to 80 nm thickness depending on the polymer film 14 density, assuming the material is evenly distributed over the transducer 42 surface. The films 44 were applied by spray coating. Table 1 summarizes the selected materials, their abbreviations, and the amounts applied to the sensors 40 in the two prototype sensor systems 10. The sensors 40 were replaced partway through the testing; the amounts of coating on the replacement sensors are also listed in Table 1.

TABLE 1

Chemically Selective Polymer Coatings Applied to the SAW Devices.

| Polymer Coating | Abbreviation | DT1[a] | DT2[a] | DT1[b] | DT2[b] |
|---|---|---|---|---|---|
| Poly (ethylenimine) | PEI | 232 | 236 | 195 | 180 |
| Fluoropolyol | FPOL | 252 | 252 | 257 | 250 |
| Ethyl cellulose | ECEL | 241 | 241 | 258 | 248 |
| Poly (epichlorohydrin) | PECH | 245 | 257 | 264 | 268 |

[a]DT1 and DT2 refer to the two prototype systems. These columns give the kHz of coating originally applied to the sensors in the sensor array.
[b]These columns give the kHz of coating applied to the sensors that were used to replace those originally installed in the prototype systems.

It was planned to utilize the signals from these four sensors 40 as follows. First, it was intended to follow the signal of the fluoropolyol-coated sensor 40 closely. A response by this sensor 40 would indicate the possibility of a nerve agent hazard. Then, using the data from all four sensors 40, the pattern recognition algorithm for nerve agent classification would decide if a nerve agent was actually present. If so, an alarm would be indicated and the intensity of the fluoropolyol-coated sensor 40 response would be used to determine the level of the hazard (high, medium, or low warning).

A similar approach would be used in blister agent detection, following the signal of the blister agent sensitive sensor 40 to indicate the possibility of a blister agent hazard. The other three sensors 40, including the fluoropolyol-coated sensor 40, would provide data to create a pattern for evaluation by the algorithm for blister agent classification. This algorithm would decide if a blister agent was actually present and decide if an alarm was indicated.

In practice, it was found that the fluoropolyol-coated sensor 40 was the most sensitive sensor 40 for nerve agent detection as expected. Both the ethyl cellulose and poly-(epichlorohydrin) coated sensors 40 proved to be useful in blister agent detection and classification. Ethyl cellulose-coated sensors 40 were more selective, but poly(epichlorohydrin)-coated sensors 40 were more sensitive and faster to respond. The difference in response times is likely due to the difference in physical properties noted above. Poly(ethylenimine)-coated sensors 40 proved to be extremely useful in trouble-shooting the sampling system during the fabrication and initial testing of the prototypes (it was very good at detecting humidity changes due to leaks in the sampling system as described above), but it was not required for either of the pattern recognition algorithms. The classification algorithms were ultimately done using only the data from the other three sensors 40.

Figure 5:
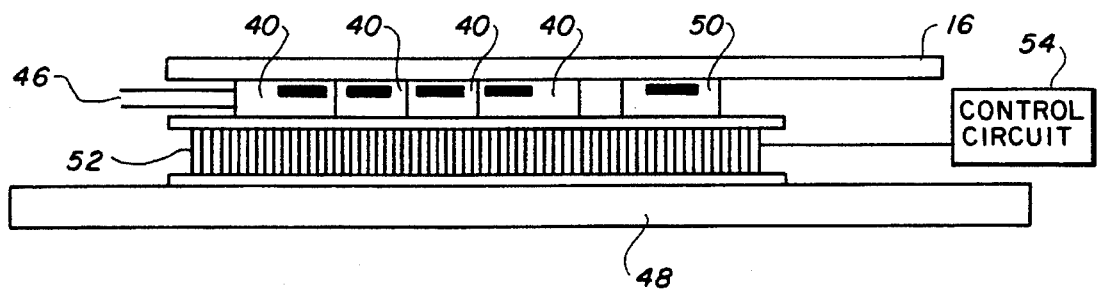
FIG. 5 is a schematic side elevational view of an array of the sensors of FIG. 4.

The four SAW sensor array 14 configuration is shown schematically in FIG. 5. Four 158 MHz single delay line SAW sensors 40 on separate chips are coated with chemically selective thin polymer films 44, each sensor with a different polymer. The sensors 40 are packaged in two flatpacks, two sensors per flatpack. Each package has inlet 46 and outlet 48 tubes for gas delivery. The two packages are connected in series with tubing. For simplicity, FIG. 5 shows the four sensors in a single package. A separate uncoated 158 MHz single delay line sensor 50 is packaged in a separate sealed flatpack. An oscillator circuit 16 is associated with each of these five SAW sensors 40. The reference sensor 50 provides a constant reference frequency. This frequency is fanned out and mixed with each of the four sensor frequencies to provide four low frequency difference signals in the range of a few hundred kHz. Low frequency difference signals are desirable because they can be easily counted with simple TTL electronics. The four sensors 40, reference device 50, oscillators 16, and mixers (not shown) are all located on one printed circuit board. In order to maintain a constant operating temperature of the sensors 40, a temperature control system 18 is provided which is descibed in detail below.

Temperature Control System

As stated above, temperature control system 18 is provided for actively controlling the temperature of sensors 40. In a preferred embodiment, a thermoelectric cooler 52 is utilized to obtain stable baselines and reproducible sensor responses.

The sensors 40 and 50 are maintained at a single temperature (30° C.) by placing all the sensor packages in contact with a single thermoelectric cooler 52 and a thermocouple (not shown). A control circuit 54 monitors the temperature and adjusts the cooler power to compensate for the heat generated by the electronics. Once the system 10 is warmed up, the sensors 40 and 50 temperatures are constant. Variations in sensor temperature are undesirable for two reasons. First, vapor sorption by the polymer coatings 14, and hence sensor responses, are highly temperature dependent. Therefore constant sensor temperatures are required to obtain reproducible response levels. Second, temperature variations contribute to baseline drift. The thermal expansion of the polymer on the device surface causes sensor frequency to vary substantially with temperature. In the absence of a polymer coating, the frequency of the packaged device still varies with temperature, although to a lesser degree.

It should be pointed out that temperature compensation schemes such as the dual delay line SAW configuration do not compensate for the temperature dependence of vapor sorption, nor do they compensate for baseline drift due to polymer thermal expansion. Consequently it is best to actively thermostat the sensors by the control circuit 54 as described. In addition, with active temperature control, there are no compelling reasons to fabricate sampling and reference devices on the same chip as in the dual delay line configuration. Therefore, the reference sensor 50 is seperated as described above. In the chosen configuration, the reference frequency is not perturbed by vapor adsorption on its surface, as can happen with dual delay line devices. In addition, there is no possibility of direct cross-talk of two sensors fabricated on the same chip, which can contribute to baseline instability with dual delay line devices.

Microcontroller

One or more microcontrollers or microprocessors 22 are used to control the sampling system 10, to collect and process frequency data, and to implement the pattern recognition algorithm (discussed below) to determine if a hazard is present. Decisions about the presence or absence of hazards can be displayed on a panel on the sensor system, used to activate an alarm 56, and/or communicated over a serial output line (not shown). The primary sensor data are also available as output on the serial line 58.

Prototypes have been produced which contain two microprocessor 22 boards for system control and data analysis. Second generation prototypes, which constitute the presently preferred embodiment, contain a single more powerful microcontroller 22 board to perform these functions, and a numeric keypad (not shown). The control circuitries of the second generation prototypes are also improved over those of the first generation prototypes, and a simpler, more flexible power supply is used. Either 115 VAC or 12–15 VDC can be used to power the second generation prototypes. The sensors 40 and microcontrollers 22 utilized by both prototypes are commercially available from Microsensor Systems, Inc., Springfield, Va.

The electronics of the system futher include the oscillator board 16 for the four SAW sensors 40, frequency counters 20, control circuitry for the valves and pumps, a control circuit 54 for the thermoelectric cooler 52 which maintains the sensor 40 temperatures, control circuits (not shown) for the thermal desorption of the preconcentrator tubes 28, serial data output port 58, a fan (not shown), and a display 56. Frequencies from the SAW oscillators 16 are counted by frequency counters 20 on a sensor interface board (not shown).

Pattern Recognition Algorithm

Pattern recognition methods are used to evaluate the information provided by the array 14 of sensors 40 and constitute a key aspect of the invention. As an information processing method, it is important to remember that the results achieved are dependent on the quality and quantity of the information provided. When pattern recognition methods are applied to vapor detection using sensor arrays 14, the information is encoded in the numerical responses of the individual sensors 40. Therefore it is important to use sensors 40 that provide consistent, high quality information. SAW vapor sensors meet this requirement. For a more detailed discussion of this point reference is made to the detailed description of the sensor arrays set forth above.

Pattern recognition analysis can be done using either statistical multivariate methods or neural network methods. Currently it is easier to implement a statistically derived algorithm than a neural network on a small microcontroller board in a sensor system 10 and the former method is utilized in the preferred embodiment of the invention. The development of an algorithm first requires that a training set of vapor response data be collected for analysis. This data set must include vapors to be detected, as well as a variety of potential background vapors that the instrument must learn to ignore to avoid false alarms. The training set must be properly balanced to avoid random classifications and so that the algorithm that is developed will be reliable in the field. The better designed the training data set and the more data available, the better the algorithm. Once the training set has been collected and the sensor responses have been extracted, then an algorithm can be developed to carry out this method.

The final algorithm consists of a linear discriminant and is mathematically quite simple. It can be easily programmed into the on board microprocessor 22 of the sensor system 10. Separate algorithms are developed for nerve and blister agent classification as discussed above.

In considering the use of sensor arrays and pattern recognition for the detection and correct classification of hazardous vapors, it is important to understand that these techniques do not operate by checking the observed pattern against a library of vapor signatures. Thus, it is not necessary to have a signature of a potentially interfering vapor stored in memory in order to discriminate against it. Pattern recognition techniques plot out the pattern of responses to a vapor challenge as a point in N-dimensional hyperspace (called feature space), where N is the number of sensors 40, and each of the N-axes represents the response of the sensor 40 associated with that axis. Any vapor which is dissimilar to the target analyte, according to the criteria by which the sensors respond to vapors, will be plotted in a different region of feature space than the target analyte. Thus, dissimilar vapors can be successfully discriminated against even if they have not been tested in the training set. In addition, this method does not require that the calibration curves for all vapors be linear in order to obtain correct classification and discrimination. In this regard, it is noted that none of the prior art cited in the introductory section above is able to accomplish this. These are some of the reasons why these techniques can be very valuable in a field environment where unknown vapors may be present in the background.

These features of pattern recognition techniques also illustrate why it is important to choose sensor coating materials 14 carefully: a diverse set of sensors 40 with strong, selective, and uncorrelated responses will more effectively spread different vapors out in feature space, facilitating discrimination. (For a more detailed discussion on this point, reference is made to the sensor array section above.) In addition, having independent sensors also adds stability to quantitative analysis.

Training Set

Figure 6:
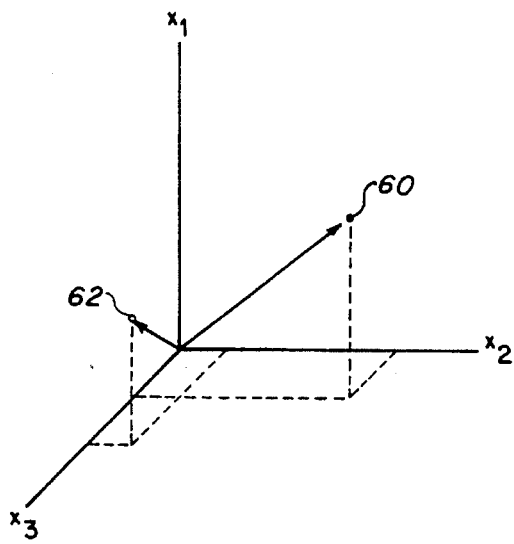
FIG. 6 is a graphical representation of a three-dimensional space which graphs the reponse of the sensors of FIG. 4.
Figure 7:
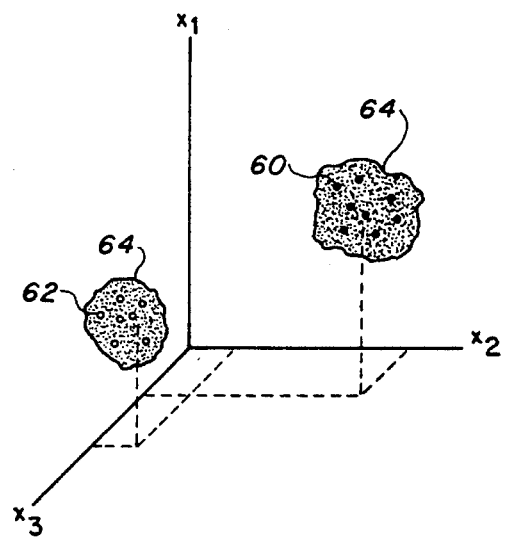
FIG. 7 is a graphical representation of the clustering of objects in the three-dimensional space of FIG. 6.

The sensor responses encode chemical information concerning each vapor in a numerical form. Each sensor defines an axis of a coordinate system in space, often referred to as "feature space". The dimension of the coordinate space depends on the number of sensors used, for example two sensors define a plane. Each compound or vapor can be thought of as a point whose position in space is defined by the values produced by each sensor. The three-dimensional example in FIG. 6 shows two vapor responses 60 and 62 for three sensors 40, which form the axes $x_1$, $x_2$ and $x_3$, respectively. If the sensors 40 are selected appropriately, the positions of the vapors depend on their chemical properties. Further, related objects tend to cluster in a region of space 64 defined by the sensor responses as depicted in FIG. 7. Two- and three-dimensional studies can be easily observed graphically. When more sensors are required to adequately describe a set of vapors, then more sophisticated methods of analysis are necessary.

Pattern Recognition Training Methodology

The statistical and pattern recognition methods used to develop the weight vectors in this invention are implemented in a computer software system known as ADAPT, an abbreviation for Automated Data Analysis and Pattern Recognition Toolkit. The software was run on the VAX 11-750 at the Naval research Laboratory (NRL). This set of computer software contains a wide variety of techniques necessary for performing complex compound-response analysis. The ADAPT software system was developed at Pennsylvania State University and is commercially available from Molecular Design Ltd., San Leandro, Calif.

The sensor responses for each of the vapor exposures in the data set are entered in the computer and the computer generates and stores a data matrix. Each row in the data matrix can be thought of as a pattern vector:

$$X_i = (x_1, x_2, x_3, \ldots, x_n) \tag{1}$$

where $X_i$ is the pattern for vapor experiment i, and $x_j$ are the sensor responses from 1 to N sensors 40.

In general, the vapors are considered as points defined by N sensors 40 and projected onto N-dimensional space, where the coordinate system is defined by the sensors 40.

The category of pattern recognition methods used in this system 10 are classification methods, which are also considered supervised learning techniques because the methods are given both the data and the correct classification results. With this information, the methods generate mathematical functions to describe the clustering 64 discussed above. There are two basic ways for classification methods to operate: (a) parametric, and (b) nonparametric.

Parametric techniques use statistical information based on the underlying data to define the boundaries of the clusters 64. Their performance is based on the assumptions made concerning the statistical characteristics of the data. The nonparametric techniques use mathematics to define the area between the clusters 64.

Figure 8:
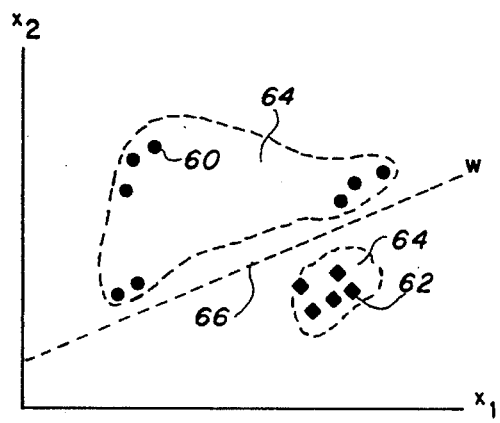
FIG. 8 illustrates a two-dimensional space which shows a line, defined by a linear discriminant function, separating two clusters.
Figure 9:
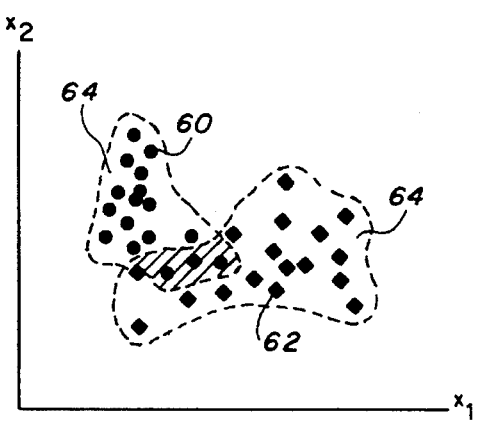
FIG. 9 illustrates a two-dimensional space which shows two clusters which may not be defined by a linear discriminant function.

Learning techniques are used to train the algorithm on the correct classification results. A discriminant function is found that separates one class or cluster 64 from another. The width of the discriminant function is a measure of the separation between the clusters 64. For example, FIG. 8 illustrates a two-dimensional N-space which shows a line 66 separating the two clusters 64, whereas, in the three-dimensional case, the methods define a plane which bisects the two clusters 64. These discriminant functions are called linear discriminants. If two clusters 64 are not separable as in FIG. 9, a boundary cannot be defined that will completely identify the vapors of interest because of the overlap of the two clusters 64 which is indicated by the shaded region in FIG. 9.

The ADAPT software provides an excellent method for analyzing large sets of compounds. An extremely useful feature, made possible by the ADAPT software, is the use of many classifiers. The different classification methods provide greater insight to the study. The various visualization methods allow the chemist to see the analysis from different perspectives. The greatest advantage is the ability to pass information from one classifier to another using weight vectors. Therefore, combinations of classifiers can be used, thus combining their strong points. In this manner, the best results are deduced more readily.

As stated above, parametric and nonparametric programs are used to define the borders of the clusters 64 by defining discriminant functions. Examples of parametric and nonparametric programs used in these studies are described below.

The Bayes decision function for normal (Gaussian) pattern is:

$$d_k(X) = \ln p_k - 0.5 \ln |C_k| - 0.5[(X-m_k)'C_k^{-1}(X-m_k)] \text{ for } k=1,2 \tag{2}$$

where p is the a priori probability for class k, $C_k$ is the covariance matrix for class k, X is a pattern vector, and $m_k$ is the mean vector for class k. A given pattern vector, X is assigned to the class where $d_k(X)$ is greatest. This discriminant assumes a multivariate normal distribution of the data. Bayes linear assumes all the covariance matrices are equal, $C_1 = C_2$ for classes 1 and 2. The equation above simplifies to:

$$d_k(X) = \ln p_k + X'C^{-1}m_k - 0.5 m_k'C^{-1}m_k \text{ for } k=1,2 \tag{3}$$

The decision boundary between the classes is defined by subtracting $d_2(X)$ from $d_1(X)$ and setting the function equal to zero. When the covariance matrices are equal, the decision surface is linear in the variables describing a hyperplane. To achieve the best classification results, each sensor response is multiplied by a constant. Because the decision surface is linear, the resultant weight vector generated by this classifier can be stored and used in other classifiers. All of the nonparametric classifiers can accept weight vectors from other routines and they improve classification results by iteratively updating the weight vector. Each classifier uses different criterion to generate and alter the weight vectors. Therefore, weight vectors can be improved by passing them between classifiers because this technique can take advantage of the variety of methods available. For further information on Bayes decision functions, see J. T. Tou and R. C. Gonzalez, *Pattern Recognition Principles*, Ch. 5, Addison-Wesley: Reading, Mass. (1974).

One least squares classifier in ADAPT is a method using an adaptive least square (ALS) technique. The method was developed for the discrimination of ordered categorical data. The routine has the advanatage over all the other classifiers in that it simultaneously considers up to ten classes or clusters 64 and produces a single discriminant function which can designate the compounds into various classes or clusters 64.

The ALS method defines an equation:

$$L = X \cdot W \tag{4}$$

where X is the data matrix, W is the weight vector, and L is the discriminant score. The starting scores are defined by the equation:

$$a_j = 2\left(2\sum_{i=1}^{j-1} n_i + n_j\right)/n - 2 \tag{5}$$

where i and j are two different classes, $n_i$ and $n_j$ are the number of compounds in that particular class, and n is the total number of compounds. The cutoff points between the classes are the midpoints between the a values and are assigned the symbol b. A weight vector can be input from another classifier or initialized within ALS. The weight vector is initialized in ALS by assigning the starting scores to an array, S and by performing the matrix computation shown below:

$$W = [(X'X)^{-1}X']S \tag{6}$$

where X' is transpose of the data matrix. Computation time is minimized by performing the bracketed calculation once. Equation 4 is evaluated using the appropriate weight vector. The resulting L values are compared to the b values for class designation. For example, if $L < b_1$, it belongs to class 1 and if $b_1 < L < b_2$, it belongs to class 2. These results are compared to the known results. If a compound is misclassified, a new weight vector is developed by adding a correction factor to the L value for the compound missed and placing that value into the element in the array S corresponding to that compound. The corrected weight vector is inserted into equation 4 and the process is repeated until all the compounds are classified correctly or a given number of iterations has been reached. The correction factor used in ALS is shown below:

$$C = \frac{0.1}{(\alpha+d)^2} + \beta(\alpha+d)^2 \quad (7)$$

where $\alpha$ and $\beta$ are constants empirically selected by the chemist and d is the absolute difference between L and closest b. The ALS method has proven to be a powerful classifier because the chemist can select constants to be used in the correction factor. This method gives the user more control over the actual size of the correction factor as the process proceeds. For more information on the least squares classifier, see I. Moriguchi, K. Komatsu and Y. J. Matsushita, "Adaptive least squares method applied to structure-activity correlation of hypotensive N-alkyl-N"-cyano-N'-pyridyguanidines," *Med. Chem.*, Vol 23, p 20–26 (1980).

In addition to ALS, the linear learning machine classifier was used. This is the simplest of the nonparametric classifiers. The linear learning machine is an iterative algorithm that develops a linear decision surface through error correction feedbacks. If the sensors are carefully chosen the two classes should be clustered in two separate regions in space. The object is to fit a linear decision surface between the clusters. The compounds are designated positions relative to the decision surface by performing a dot product calculation between the pattern vectors and the weight vector.

When classifications are to be made using nonparametric linear discriminant functions, much thought needs to go into the data acquisition. The data set is divided into categories; in this study only two classes were used, vapors of interest and potential interference vapors. To avoid random classifications, it is important to have at least three observations (vapor experiments) for each variable (sensor) to be tested, and the number of variables cannot be greater than the number of observations in the smallest class. For futher information on this point, see T. R. Stouch and P. C. Jurs "Monte Carlo studies of the classifications made by nonparametric linear discriminant functions," *J. Chem. Inf. Compt. Sci.* Vol 25, p. 45–50 and 92–98 (1985). Another study has indicated the importance of balancing the number of observations in the classes to reduce chance classifications, (see Stouch, et al., "Chance factors in nonparametric linear discriminant studies," *Quant. Struct.-Act. Relat.*, Vol 5, p. 57–61 (1986)). Two data sets should be collected whenever possible. One set is training set and should be as large as possible, and the other is a prediction set to test the classifiers developed. Because only a few vapors are in one class (the vapors of interest) and a large number of interferences are in the other class, several concentrations and mixture combinations containing the vapors of interest were used to increase the number of vapor experiments in the smaller class. In addition, mixtures were included in both classes to balance the data set by vapor experiment type as well as quantity.

When a system 10 is to be operated in the field where the concentration is unknown, a normalization method is required to produce a pattern independent of concentration, while being derived mathematically so that the concentration can be determined later. A closure option, which divides the pattern values by the square root of the sum of the squared values was used for scaling and is called pattern normalization. The method makes all the pattern vectors have a length of one: it forces all the patterns onto the surface of a hypersphere. Pattern normalization allows the data to be considered independent of concentration and sensor sensitivity to specific compounds. The vapors that give small respones are equally as important as the vapors that give strong ones, which is important in the application of pattern recognition routines.

Pattern Recognition Discriminants

Consideration will now be given to the development of the pattern recognition algorithms, wherein the term pattern recognition algorithm refers specifically to the discriminants used to distinguish hazards from other background vapors. The development of the algorithms is based on the patterns of sensor responses determined from the original test data by prior analysis (described above) and the pattern recognition methology described above. The analysis of real time data and implementation of the discriminants in real time will be separately described below.

The data from the test set was used for the algorithm development. Four pattern recognition analyses resulting in four linear discriminants are necessary. One discriminant for nerve agents and one for blister agents will respond to challenges observed in direct sampling mode, while the other two discriminants will evaluate response patterns observed in the preconcentrator sampling modes for nerve and blister agents. Software was written to consolidate the large number of data files and to transfer the information to the Chemistry VAX where the pattern recognition training software is stored and executed. Then, the data was organized into data matrices for multivariate data analysis.

A typical pattern recognition analysis study requires that the data set be divided into two classes. In the present case, Class 1 consists of the chemical agent vapor or simulant to be classified as a CW hazard, and Class 2 consists of all other vapors that must be ignored to avoid false alarms. Thus, Class 2 consists of potential background vapors, also referred to as potential interferences.

The data and the correct classification results are given to several supervised learning techniques in the ADAPT software package as described above. The classifiers are designed to generate a discriminant in one classifier and to allow that discriminant to be passed to another. A statistically based classifier as described above is used to generate the initial discriminant, which is then passed to the adaptive least square algorithm described above. Several iterations and several combinations of classifiers are used to train the data set. The resulting discriminant is passed to a classifier called the linear learning machine described above, and the data set is trained further adding thickness to the discriminant hyperplane between the two classes.

Nerve Agent Classification in Preconcentrator Sampling Mode

The algorithm development was a complex task, so it was divided into subtasks. The first subtask was the nerve agent classification using the preconcentrators. The two-minute preconcentrator data for GD, VX and DMMP as well as mixtures containing GD were organized into Class 1 and all the other vapors, including HD because it is not a nerve agent, were organized into Class 2. The nerve agent GD, also known as soman, is known chemically as pinacolyl methylphosphorofluoridate or methylphosphonofluoridic acid, 1,2,2-trimethylpropyl ester and its structure can be represented by $CH_3P(O)(F)OCH(CH_3)C(CH_3)_3$. The nerve agent VX, which has no common name, is known chemically as ethyl S-2-diisopropyl aminoethyl methylphosphorothiolate and it can be structurally represented as $CH_3P(O)(OC_2H_5)SCH_2CH_2[CH(CH_3)_2]_2$. The stimulant DMMP, or dimethyl methylphosphonate, has structure which can be represented as $CH_3P(O)(OCH_3)_2$. The blister agent HD, which is also known as mustard gas or distilled mustard, is known chemically as bis(2-chloroethyl)sulfide and it has structure which can be represented as $ClCH_2CH_2SCH_2CH_2Cl$. It should be noted that the fourteen-minute preconcentrator data was not included in any analysis. First the natural clustering of the data was observed using unsupervised pattern recognition methods and was found to be excellent using three sensors, FPOL, ECEL and PECH. PEI is used as a humidity indicator and was not included in the identification pattern. The three-sensor array data listed in Table 2, located at the end of the specification, were used as a training set to develop an algorithm to recognize the presence of nerve agent hazards. After pattern normalization to remove concentration information from the identification portion, a linear discriminant was found that could correctly identify the nerve agent in 100% of the cases. Thus, there were no false negatives. For a few vapor exposures, HD was identified as a nerve agent (i.e., caused a false positive), but none of the other Class 2 vapors were misclassified. The total recognition of both classes was 99%. The linear discriminant was further improved by increasing the boundary thickness, thus forcing the best placement of the boundary in space between the clusters. The ability to increase the thickness of the weight vector without hurting the classification result is a good indication of the excellent separation between the nerve agents and the interference vapors with this set of sensors in this sampling mode.

Nerve Agent Classification in Direct Sampling Mode

The second subtask is to identify the responses to nerve agents in direct sampling mode. For the identification of the nerve agents, the data for GD, VX and DMMP that produced a detectable response in direct sampling mode were organized into Class 1 and all the other vapors producing a detectable response, including HD because it is not a nerve agent, were organized into Class 2. This data set is shown in Table 3. It includes responses detected during 10 second intervals after first indication of a response. Consequently, some exposures are entered into the table as many as 3 times, i.e. for the first 10 seconds of response, the second 10 seconds of response, and the third 10 seconds of response. Nevertheless, this data set is much smaller than the data set in Table 2 used to develop the linear discriminant for nerve agent detection in two minute preconcentrator sampling mode because the lower concentrations of agents did not produce a detectable response in direct sampling mode. In some cases, only the FPOL sensor responded. Again, PEI was not used in the identification pattern. FPOL, ECEL and PECH comprised the three-sensor array. The data matrix was used as a training set to develop an algorithm to recognize the presence of nerve agent hazards. After pattern normalization to remove concentration information from the identification pattern, a linear discriminant was found that could identify all detectable exposures to nerve agents or simulants. In some cases the earliest indications of responses to DMMP were not classified as nerve agents, but the response produced by the sensor 10 seconds later produced the correct classification. Therefore the vapor did not go undetected, it simply required an additional 10 seconds before the correct pattern was produced. Most vapors were detected within 10 seconds, some required as much as 30 seconds to produce a recognizable pattern. None of the Class 2 vapors were misclassified.

Blister Agent Classification in Preconcentrator Sampling Mode

The third subtask was to identify the response to blister agent using the preconcentrators. One uncertainty that arose in the development of the blister agent algorithms was how to handle data collected for 1,5 dichloropentane (DCP). Originally, it was thought that DCP might serve as a simulant for HD, and in this case it should be included in Class 1 with HD. However, it was found that DCP was not an effective simulant, so it was not clear if including the DCP data would be useful. Therefore, the data was examined both ways, with and without DCP in Class 1. DCP could be excluded from consideration by defining a narrower window for blister agent peaks. DCP desorbs faster than HD. For example, a window from point 17 to 24 includes peaks for DCP. A point equals 2 seconds. A narrower window from 19–24 excludes DCP peaks, and also excludes peaks from diesel fuel that are included in the 17–24 point window.

In addition, it was found that patterns for low concentrations of HD, i.e., 0.05 $mg/m^3$, were not as consistent as those for the higher concentrations of HD. Removing these 0.05 $mg/m^3$ HD data points from the training set resulted in better algorithms (fewer misclassifications of Class 2 vapors, which reduces false alarms). In total, four algorithms were investigated, i.e., training sets with and without DCP, each with and without 0.05 $mg/m^3$ HD data, and the best results were obtained using the training set without either DCP or 0.05 $mg/m^3$ HD data. When this algorithm is applied to DCP data, allowing the wider window for examining DCP peaks, it classifies DCP as a Class 1 hazard. In this regard, DCP can serve as a qualitative simulant for HD, although it is not detected with the high sensitivity with which HD is detected.

Table 4 presents the training set data with HD at concentrations above 0.05 $mg/m^3$ and mixtures containing HD organized into Class 1 and all the other vapors, including GD, VX and DMMP, organized into Class 2. DCP data and 0.05 $mg/m^3$ HD data are not included in the training set. The data was taken from the 19–24 point window, which excludes peaks for DCP and diesel. PEI was not used in the identification pattern. FPOL, ECEL and PECH comprised the three-sensor array. After pattern normalization to remove concentration information from the response pattern, a linear discriminant was found that could identify the the training set vapors correctly in 100% of the cases. If this discriminant is applied to the low concentrations of HD (0.05 $mg/m^3$) collected in the algorithm testing, it correctly classifies half of the tests. In use for HD detection, this algorithm would be used with the 19–24 point window to get the best classification results. However, if it were desirable to use DCP as a simulant, then one could use the wider window and detect and classify DCP as a blister agent hazard. The drawback of using a wider window is that it reduces the selectivity for HD and thus creates the possibility of false alarms.

Blister Agent Classification in Direct Sampling Mode

The fourth subtask was to classify blister agents in direct sampling mode. It is not actually necessary to detect blister agent in direct sampling mode because the fastest response time required is 2 minutes, and the system can detect and classify blister agents correctly using the two-minute preconcentrator mode. However, the possibility that the system could detect and correctly classify blister agent faster than required by using direct sampling mode was investigated. Three training sets were investigated: with DCP in Class 1, with DCP in Class 2, and with no DCP data included. Inclusion of DCP in Class 2 is definitely not recommended because the resulting algorithm then misclassifies several Class 2 vapors, which would cause false alarms. The other two algorithms produced much better classification results.

It is preferred that the algorithm be developed without DCP data.

To obtain the preferred algorithm, the direct sampling data in Table 3 were reorganized placing detectable concentrations of HD, and mixtures containing HD in Class 1. All the other vapors that produced a detectable response in direct sampling were put in Class 2, except DCP data, which was excluded from the training set completely. This training set is listed in Table 5. After training, all detected exposures to HD could be correctly classified. Most of these were at 10 mg/m$^3$, although a few exposures at 2 mg/m$^3$ and one at 0.5 mg/m$^3$ produced detectable response and were correctly classified. In a few cases, the initial response to an HD exposure was not identified as a blister agent, but with 10 or 20 more seconds of exposure time correct identification was made. One diesel fuel exposure caused a detectable response in direct sampling mode and this was misclassified (false positive). Therefore, excluding DCP from consideration, only a single experiment resulted in misclassification. Normally diesel was not detectable in direct sampling at the test concentration, in either preconcentrators-on or preconcentrators-off operational mode, so the single misclassified result is spurious. Since diesel would not normally be detected it would not cause a false positive in this mode.

If this algorithm is applied to DCP data detected in direct sampling, it sometimes classifies it as a Class 1 hazard. Therefore, DCP is not an effective simulant in direct sampling using and algorithm trained to recognize HD.

This algorithm can be applied to patterns observed as soon as the first indication of a response is detected. However, it has been found, that these patterns are not as well defined as those obtained after another 20 to 30 seconds of response time. Since blister agent need not be detected in such short time periods, it is recommended that final decisions on the presence or absence of blister be delayed until 30 seconds after the first indication of a response, so that patterns are well defined and the likelihood of a false positive is reduced.

Pattern Recognition Fundamentals

The fundamental premises of pattern recognition as appied to sensor array analysis are: 1) the identity of the compound and the response of the instrument are related; 2) the identity of a compound can be adequately represented as a set of sensor responses; 3) a relation can be discovered by applying pattern recognition methods to a data set of sensor responses to tested vapors and vapor mixtures; and 4) the relation can be extrapolated to untested vapors and vapor mixtures.

Pattern recognition techniques provide the means to investigate more complex problems. Pattern recognition uses multivariate statistics and numerical analysis to investigate such clustering, and to elucidate relationships in multidimensional data sets. Using supervised learning techniques, a discriminant can be developed to distinguish between toxic vapors of interest and other vapors that may occur in the background that might cause and interference. Smart sensor systems corresponding to system 10 using pattern recognition may be adapted to specific detection problems by the choice of the discriminant developed, or by selecting different coating for the array and developing the appropriate discriminant. For a more detailed discussion on this subject reference is made to the sensor array section above.

Summary of Linear Discriminants

The linear discriminants developed are given in Table 6 for each of the studies described above. Each discriminant in this study consists of three coefficients, one for each of the sensors (FPOL, ECEL, and PECH), and a constant. The linear discriminant is also called a weight vector.

TABLE 6

| | Linear Discriminants | | | |
| --- | --- | --- | --- | --- |
| | FPOL | ECEL | PECH | Constant |
| Using Concentrators | | | | |
| Organophosphorus Vapor | 0.686 | 0.0493 | 0.291 | −0.665 |
| Organosulfur Vapor | −0.765 | −0.178 | −0.264 | 0.560 |
| Direct Sampling | | | | |
| Organophosphorus | 0.852 | −0.0244 | −0.443 | −0.278 |
| Organosulfur vapor | −0.148 | 0.0975 | 0.122 | −0.110 |

In operation, the linear discriminants are used as follows. First, the sensor frequencies are followed until a change indicating a response to a vapor is observed. The frequency shift response of each of the sensors is determined. These are pattern normalized. The normalized responses are used to evaluate the linear discriminant(s): each response is multiplied times its corresponding coefficient and these are summed with the constant. In other words, the dot product of the normalized responses and the weight vector is determined. If the result is a positive number, then the vapor is a Class 1 hazardous vapor and an alarm should be reported. If it is negative, then the vapor is ignored and no alarm is indicated.

For example, on exposure to a detectable concentration of nerve agent, the nerve agent discriminant will give a positive result. Application of the blister agent algorithm to the same responses should give a negative result, since a blister agent is not present. Similarly, if a blister agent is present, the nerve agent algorithm should give a negative result and the blister agent algorithm will give a positive result. If neither agent is present, both algorithms should give negative results.

By utilizing the above linear discriminants, the organophosphorous vapors were identified 100% of the time while some of the organosulfurous vapors were occasionally misclassified. The total recogintion of both classes was 99%.

Algorithm Validation and Prediction Sets

It is useful to validate pattern recognition algorithms by applying them to test data that were not included in the data matrices used to generate the algorithm. The latter data are referred to as the training set. The additional sets of data used to validate the algorithm are referred to as prediction sets. The system check testing provided additional agent challenge data to be used as a prediction set to see if the algorithms would correctly classify these hazards. It also included new background vapors, i.e., the inorganic vapors discussed previously. Including these in prediction set, test the ability of the algorithms to discriminate against background vapors that were not included in the training set. In addition, we used data collected at NRL to see how the algorithms would classify methyl salicylate (MES) and diethyl malonate (DEM). These compounds are sometimes used as physical simulants of CW agents, although they are poor chemical simulant and are of limited value for testing SAW sensor systems.

The data was organized into three prediction sets given in Tables 7, 8, and 9. Table 7 includes data from direct sampling mode in the system check tests and direct sampling MES data. Table 8 includes data from two-minute preconcentrator mode in the system check tests. Table 9 includes data from two-minute preconcentrator mode in other not previously used in the algorithm developement tests. The results are organized first by the hazard to be recognized, then by the vapors tested, and then by sampling mode. For each vapor, the two-minute preconcentrator mode will be discussed first. The discussion below refers only to the data in the system check, and not to the data in the algorithm testing, discussed earlier.

System Check Nerve Agent Classification

In two-minute preconcentrator mode, all challenges to GD (0.5 and 0.05 $mg/m^3$) in the system check were correctly classified by the nerve agent algorithm, as were the mixtures of GD (at 0.5 $mg/m^3$) with bleach, ammonia, and sulfur dioxide. The only case where GD was not correctly recognized was in a mixture with HD. In this case however, the HD was correctly identified and an alarm would occur for blister.

In direct sampling mode, GD is generally not detected at 0.5 $mg/m^3$. Consequently, no data for GD alone is in the direct sampling mode prediction set (Table 7). Mixtures of GD (0.5 $mg/m^3$ with ammonia did produce responses, but they are not recognized by the algorithm as nerve agent. This is not surprising since GD is near the limit of detection. Similarly, sensor responses from mixtures of GD (0.5 $mg/m^3$) with HD were not classified as nerve gas.

In two-minute preconcentrator mode VX was detected and correctly classified at 0.5 $mg/m^3$, 0.05 $mg/m^3$ and even at 0.0005 $mg/m^3$. In direct sampling VX was detected at 0.5 $mg/m^3$ and these responses were correctly classified as nerve agent hazards.

DMMP was detected and correctly classified as a nerve agent hazard at 1 and 0.1 $mg/m^3$ in two-minute preconcentrator mode. In direct sampling DMMP is detected at 1 $mg/m^3$ is correctly classified as a nerve agent hazard.

In two-minute preconcentrator mode, HD, DCP, and mixtures containing HD were not classified as nerve agents, indicating that they do not cause false positives for nerve agents. Ammonia and sulfur dioxide were not detected in two-minute preconcentrator mode and therefore do not cause false positives. In some cases the bleach exposures did cause false positives for nerve agent.

HD, DCP, and ammonia were not classified as nerve agents in direct sampling, indicating that they do not cause false positives for nerve agent. Bleach and sulfur dioxide did not cause responses in direct sampling mode and so no responses for these vapors are in the direct sampling prediction set. Thus, they do not cause false positives.

In two-minute preconcentrator mode, MES desorbs very slowly from the Tenax. Towards the end of the desorption time the sensor signal (of FPOL, for example) rises significantly, but a peak does not occur before the sampling mode is switched back to direct sampling. Consequently, this late rise in signal is not detected, since a peak must form before our data analysis procedures indicate a vapor has desorbed. Some weak peaks were observed prior to the end of the desorption time. Although these may not be due to MES (possibly they are due to impurities), they were entered into the data set. They were not classified as nerve agents. MES was not detected in direct mode at 0.16 or 1.4 $mg/m^3$. It was detected in direct mode at 20 $mg/m^3$, but it is not classified as a nerve agent by the nerve agent algorithm. These results confirm the point that MES is not a good nerve agent simulant for SAW sensor system evaluation. The SAW sensors are not nearly as sensitive to MES as they are to nerve agents, the desorption characteristics of MES on the preconcentrator tubes are different from those of nerve agents, and thus the algorithms do not recognize MES as a nerve agent.

DEM is detected in two-minute preconcentrator mode at 0.11 and 1.1 $mg/m^3$. Peaks occur at 30 to 36 seconds. DEM at 1.1 $mg/m^3$ is classified as a nerve agent hazard, but at the lower concentration it is not. DEM was not detected in direct sampling mode at 0.11 or 1.1 $mg/m^3$, and so no responses for this vapor is in the direct sampling prediction set. We conclude that DEM is not a good simulant for nerve agents for SAW sensor evaluation, since SAW sensors are not nearly as sensitive to DEM as they are to nerve agents. Additionally, the algorithms do not classify low concentrations of DEM as a nerve agent.

System Check Blister Agent Classification

This section included both the results in two-minute preconcentrator mode and results in direct sampling mode, even though it is not necessary to detect and classify blister agents in direct mode to meet the 2 minute response time desired for this agent (as discussed in Part 1). This section only reports the results for the application of the preferred blister agent classification algorithms. The other algorithms investigated were also applied to the prediction sets, but the results will not be discussed here.

In two-minute preconcentrator mode, the preferred blister agent algorithm (developed without DCP or 0.05 $mg/m^3$ HD data in the training set) correctly classified all samples containing HD in the system check (HD at 2, 0.5 and 0.05 $mg/m^3$), including those where HD was mixed with other vapors (HD at 2 $mg/m^3$). The GD/HD mixture was classified as a blister agent. It is noteworthy that in these tests, the algorithm was successful in classifying even the lowest concentrations of HD. In direct sampling the preferred blister agent algorithm (trained without DCP in the training set) correctly classified the HD and HD containing mixtures that could be detected in direct sampling mode. The GD/HD mixture was detected and classified as a blister agent in direct sampling mode.

The blister algorithm for two-minute preconcentrator mode classifies DCP as a blister agent if the peak window is wide enough to include DCP peaks. The algorithm for blister agent classification in direct sampling classifies detectable DCP exposures as blister agent.

Exposures to nerve agents GD or VX, or simulant DMMP, or mixtures of GD with non-agent vapors are not classified as blister agents by the two minute preconcentrator mode blister agent algorithm. Similarly, nerve agent or nerve agent simulant exposures detected in direct sampling mode were not classified as blister agents by the direct sampling mode blister agent algorithm, with one exception. The GD/ammonia mixture was misclassified as a blister agent. Thus, nerve agents do not cause false positives for blister agent in the system check, except for the mixture with ammonia.

Bleach is sometimes misclassified by the blister agent two-minute preconcentrator mode algorithm (10 of 15 experiments were misclassified). Sulfur dioxide and ammonia were not detected in this mode and hence do not cause false positives. The direct sampling blister agent algorithms misclassify ammonia as a blister agent hazard, but bleach is not detected in direct sampling, and sulfur dioxide is not detected.

As previously discussed in the section on nerve agent classification in the system check, MES is slow to desorb from the preconcentrator tube. However, some small peaks of indeterminate origin at points 18–20 were seen in MES testing at high concentrations, and these were classified as a blister agent by the two-minute preconcentrator blister agent algorithm. MES (at 20 mg/m$^3$) is not classified as a blister agent by the direct sampling algorithms. Generally, MES is not a good simulant for blister agents. The SAW sensors are not nearly as sensitive to MES as they are to HD, the desorption characteristics of MES on the preconcentrator tubes are different from those of HD, and the algorithms do not consistently recognize the MES as a blister agent.

DEM in dry air is usually (in 8 of 10 tests) classified as blister agent hazard by the two-minute preconcentrator algorithm. However, in medium humidity air, DEM ws not classified as a blister agent even at higher concentrations. DEM is not detected in direct sampling at the tested concentrations, and hence is not seen as a blister agent in this mode. It is concluded that DEM is not an effective simulant for blister agents.

Summary of the Algorithm Results as applied to the System Check Data

The algorithm developed from the training set data were excellent at recognizing agent hazards in the system check testing. All detectable exposures containing nerve agents or nerve agent simulants, including those in mixtures, were classified as nerve agents except the GD/HD mixture. Similarly, all detectable exposures containing blister agents, including blister agent in mixtures, were correctly classified as blister agents, including the GD/HD mixture.

The data collected from tests against bleach indicate that this vapor might cause false alarm problems. However, given the uncertaintains in test procedures used to generate gas streams containing bleach, and uncertainties in the concentrations actually generated, it is not certain that this vapor would actually be a problem in the field.

Ammonia caused a misclassification problem in efforts to detect blister in direct sampling mode, but it is not necessary to detect blister agents in direct sampling mode. Ammonia mixed with GD was incorrectly classified as a blister agent in direct sampling mode. However, it is emphasized that ammonia was tested at unrealistically high concentrations. 50 mg/m$^3$ is nearly 70 ppm, and the threshold limit value (TLV) for ammonia is 25 ppm. At 25 ppm of NH$^3$, people are already uncomfortable, so it is very unlikely that anyone would be present where the ammonia concentration is 70 ppm. We would not expect ammonia to be detected at all at realistic concentrations, and therefore it would not cause a false positive for blister agents in direct sampling mode. Nor is it likely that the GD/ammonia mixture would cause problems if the ammonia concentration were lower.

The vapors tested as potential simulants (DCP, MES, and DEM), but which are in reality poor simulants, produced varying results depending on the algorithm and sampling mode. These compounds are not expected to be present in the background at any significant concentration and so should not pose any false alarm problem.

SUMMARY OF ALL PATTERN RECOGNITION RESULTS

In this section a discussion is provided of a combination of the results from the algorithm and system check testing.

The results are summarized in Table 10. The discussion below concentrates on the results for nerve agents GD and VX, nerve agent simulant DMMP, blister agent HD, and all potential background vapors specified. The results for DCP, DEM, and MES are not considered since they are neither agents nor specified background vapors, nor are they effective simulants.

Detectable concentrations of nerve agents GD and VX, and simulant DMMP are always classified correctly. In other words, if the test concentration produces a measurable response above certain threshold signals defined in the data analysis, the nerve agent classification algorithms always correctly identify the hazard (no false negatives). Moreover, correct classification was achieved even when the agent was present in mixtures, with one exception. GD was not correctly classified in a mixture with HD.

None of the non-agent Class 2 vapors caused false positives for nerve agents except bleach where the results were very inconsistent. In a few tests, HD caused a false positive for nerve agent.

Detectable concentrations of blister agent in direct sampling, and concentrations of blister of 0.5 mg/m$^3$ or higher in two-minute preconcentrator mode, were always correctly classified (no false negatives). At 0.05 mg/m$^3$ in two-minute preconcentrator mode, blister agent was usually classified as a hazard. Moreover, correct classification was achieved even when the blister agent was present in mixtures, including the mixture of HD with GD.

None of the non-agent Class 2 vapors caused false positives for blister agents except bleach (in two-minute preconcentrator mode) where the results were very inconsistent, and ammonia (and ammonia/GD mixture, both in direct sampling mode) where the test concentrations were unrealistically high. Furthermore, false positives observed in direct sampling mode are not significant since it is not necessary to look for blister agent in direct sampling mode to meet the goal of a response to blister in two minutes.

Nerve agents and nerve agent simulants do not cause false alarms for blister agent.

In summary, the ability of these SAW sensor array detectors to detect and identify agent hazards without false alarms to a variety other potential background vapors is excellent.

Real Time System

The pattern recognition algorithms described above involved the analysis of "pre-processed" sensor responses. These responses had been determined from prior analyses of the original sensor frequency data as a function of time and system sampling mode. In a final fielded detector the frequency data must be processed in real time to determine the sensor responses. Then the pattern recognition algorithm must be applied immediately to determine if a hazard is present. Therefore, it is necessary to develop an algorithm to analyze the data in real time and determine the responses of the individual sensors in order to generate a pattern to pass to the pattern recognition algorithm. These calculations can be done either by a separate microcomputer receiving real time frequency data from the instruments via the serial port or by the microcontroller built into the instruments.

In the discussion below, reference is made to the analysis of the real time frequency data as the signal analysis algorithm. The pattern recognition algorithm is then the linear discriminant that is applied to the pattern generated by the signal analysis algorithm. The signal analysis algorithm developed for use in real time must closely reflect the data analysis methods used to analyze the data and produce sensor response matrices for the original development of the linear discriminants.

Currently, in the laboratory, the algorithms or computer software are developed and implemented on a microcomputer. The algorithm can be applied to data from the prior testing stored on disk, or to real time data obtained by a connection to the serial port of an operating prototype. The next step would be to condense this code, eliminating the bells and whistles that help in the algorithm development process, and install it on the system microcontroller board. The microcontroller board features a full featured BASIC language with battery-backed RAM and interrupt capabilities; programs can be downloaded into this RAM via the serial port. When installed on the microcontroller board, the signal analysis algorithms and recognition algorithms must be coordinated with the code that commands the components of the sampling system and reads the frequency data.

The signal analysis algorithm has separate methods for handling the frequency data generated in each sampling mode. Each sampling mode has its own pattern recognition algorithms as well.

The signal analysis algorithm is easiest to describe for the data from the two-minute preconcentrator mode, so this will be described first. Two-minute preconcentrator mode begins with a valve switch at point 5 in a two-minute cycle. The heater begins to desorb the sample at point 10. It will be remembered that data points are taken every 2 seconds. The baseline for each sensor is determined in this time interval, using an average of the frequencies at points 7, 8, and 9. The data immediately at the valve switch, e.g., at points 5 and 6, are not used in this baseline determination because frequency instabilities (spikes) sometimes occurred on valve switching and the baseline sometimes shifted slightly at valve switching.

Once the baselines of the sensors are determined, the algorithm begins following in two ways, one for nerve agent detection, and one for blister agent detection. For nerve agent detection, the algorithm follows the signals from the FPOL sensor looking for peaks in a window between points 16 and 27 inclusive. The FPOL sensor is defined for present purposes as the primary sensor in this analysis, and a peak on the FPOL sensor as a primary peak. A peak is defined by three points where the central point is higher than the points on either side, and the peak height is greater than 50 Hz. If a primary peak is found, the algorithm then looks for corresponding peaks on the PECH and ECEL sensors, allowing for the possibility that the peaks on the other two sensors may not occur at the identical point. It looks for peaks within +/−3 points of the FPOL peak. Therefore, once the primary peak is located, which occurs 1 point after the peak actually occurs, the algorithm waits for an additional 2 points before searching for the corresponding peaks from the other two sensors. The heights of these three peaks define the pattern that is then analyzed by the linear discriminant for nerve agent classification in the two-minute preconcentrator sampling mode (i.e., passed to the pattern recognition algorithm). The pattern recognition algorithm determines if the pattern indicates a nerve agent hazard. If so, then the height of the FPOL sensor peak can be used to decide if the nerve agent hazard is high, medium, or low.

Blister agent detection in two-minute preconcentrator mode is performed similarly using ECEL as the primary sensor and looking for peaks in a window between points 19 and 24 inclusive. This analysis is performed in real time along with the nerve agent analysis. It is noted that the analysis can also be carried out using PECH as the primary sensor instead of ECEL. ECEL was chosen because it is more selective.

It is noted that a number of parameters can be varied to influence the performance of the signal analysis and recognition algorithms in a preconcentrator mode. One can define a smaller or larger window. As quality control and manufacturing consistency improve, such that desorption times are more consistent from instrument and more consistent after component maintenance or replacement, the window can be narrowed with an expected increase in the certainty of the agent identification. One can increase the minimum peak height to increase the reliability, i.e., reduce the likelihood of a false alarm at the expense of a slight decrease in sensitivity. For blister agent detection, for example, our sensitivity is much greater than required for many purposes, and it would be reasonable to increase the minimum peak height. The method of determining peaks can also be modified. If instruments were made that collected frequency data every one second, instead of every two seconds, then more points could be used to define a peak, reducing the possibility that noise or spikes will cause spurious peaks. If the sensors comprising the array were all in the same package (so that they would be exposed to the vapor simultaneously), and if they all had similar response time characteristics, then peaks on all sensors would occur at the same time, and after finding a peak on the primary sensor, the corresponding peaks on the other sensors could be found in a smaller range around the time of the primary peak. An additional possibility is to identify a peak by its width as well as its height. This could also help to filter out spikes in the frequency data in preconcentrator sampling mode.

The development of the signal analysis algorithms for the direct sampling mode is conceptually more complicated than the algorithms for two-minute preconcentrator mode because the baseline is less well-defined. In a preconcentrator mode the baseline is clearly defined as the frequency prior to delivering the vapor sample via thermal desorption. In direct sampling one does not know in the field when the sample air is clean and when it is dirty, and so one must develop a rationale for assigning baseline frequencies before looking for responses. These baseline frequencies may drift.

By comparison, baselines are readily defined in the laboratory because the test gas streams are known and controlled. The test gas is modulated between clean humidified air and humidified air containing the vapor. Therefore, one simply defines the baselines as the signals are modulated in this fashion because drift is much slower than the response that occurs on a sudden change in vapor concentration. Field instruments could be designed to modulate the test gas between clean air and sample air by including consumable air scrubbers in the system. However, such methods were not used in the design of the invention.

A rationale for defining the baseline can be developed by first asking why sampling in the direct mode is provided for in the first place. The two-minute preconcentrator mode is already sufficient for detecting and correctly classifying low concentrations of nerve agents and all concentrations of blister agent vapors. In addition, if a low concentration is slowly increasing, this will be noted by the analysis of the data from the preconcentrator mode. Sampling in direct mode is only required to detect and rapidly report sudden large concentrations of nerve agent. Precise quantification of the nerve agents levels is not required. If quantitative results are desired, it is not necessary to have the information immediately. One only needs the alarm rapidly. One could wait for the two-minute preconcentrator results to obtain the quantitative results, where the definition of the baseline is more straightforward.

This definition of the role of the direct mode simplifies the analysis process. One need only look for sudden changes in signal levels, and determine responses from those changes. Therefore, the data in direct sampling mode is handled by assuming that the air does not contain a hazard during startup. The sensor baselines are defined as the frequencies obtained under these conditions and these baseline values are stored for future use. If there is some question about the initial cleanliness of the air, one could simply put a scrubber on the system inlet to insure the air is clean during the initial startup. Such a startup capability could even be built into the instrument.

Signals are determined by comparing sensor frequencies during direct sampling with the stored baseline frequencies. To compensate for slow baseline drift, however, the baselines must be periodically updated. The results from the preconcentrator sampling mode are used to decide if the sample air contains any hazards. If not, the frequencies obtained in the preceding direct sampling mode can be taken as baseline frequencies.

Another approach that can be taken is to simply watch the direct sampling mode sensor frequencies to look for sudden signal increases. When such increases occur, they would indicate a sudden change in conditions, and a pattern could be taken for evaluation by the pattern recognition algorithm.

Reading the Data Output. The system 10 generates a new data output every two seconds. This output includes the cycle and point numbers and the frequencies of the four sensors in the array. The time needed to read the data output and to do all signal analysis and pattern recognition testing is less than two seconds. No data is ever lost even if several pattern recognition tests are required. The sequence of events is as follows.

1. wait for new data output
2. data is read and filtered
3. testing phase
4. wait for new data point
5. repeat After the data output is read it is saved so that it can be accessed by cycle number, point number, and sensor. The sensor system generates seven cycles of sixty points before starting over at cycle 1. The most recently collected 420 points are always stored and are available for calculations.

There are several operations and tests that are made in the testing phase. Some operations are only done at specific points of the 60 point cycle. Other operations are done after every point. The tests are described below. Tests for nerve agent are done in both preconcentrator mode and direct sampling mode. In the current implementation referred to above, tests for blister agent are only done in preconcentrator mode, since response times faster than two minutes are not required.

Filtering the Data. The first generation prototypes put spikes into the data on a random basis. To remove these spikes, the data is filtered as it is collected. If a point is x Hz above the previous point and is also x Hz above the following point it is replaced by the average of the previous and following points. If a point is y Hz below the previous point and is also y Hz below the following point it is replaced by the average of the previous and following points. The appropriate values for x and y are determined by examining the experimental data and the characteristics of the spikes.

Important Variables. Several variables are used to store important information which is either used in the tests or is used to determine if a test should be done.

f(cycle %,ch %,pt)—three dimensional array that holds the data for the most recent 7 cycles.

FPOLpeak %—stores the point number for an untested FPOL peak for the preconcentrator data. The value will always fall between 16 and 27 or will be zero indicating that there are no untested peaks.

ECELpeak %—stores the point number for an untested ECEL peak for the preconcentrator data. The value will always fall between 19 and 24 or will be zero indicating that there are no untested peaks.

heightFPOL—stores the height of a FPOL peak found in the preconcentrator data heightECEL—stores the height of a FPOL peak found in the preconcentrator data FPOLamb %—stores the point number for an untested FPOL response in the direct sampling data. The value will always fall between 35 and 55 or will be zero indicating that there are no untested responses.

Operations Performed Only at Specific Points

POINT 1—the variables FPOLpeak %, ECELpeak %, FPOLamb % are set to zero indicating that no peaks or responses have been detected in the current cycle.

POINT 5—the baselines for the ambient tests of this cycle are set. The baselines are calculated as the average of the current values of points 1–5. The averages are stored in the variables baseAmbFPOL, baseAmbPECH and baseAmbECEL. The standard deviation of these values are also calculated and stored in the variables sdFPOL, sdECEL and sdPECH.

POINT 9—the baselines for the concentrator tests are calculated. The baselines in this case are the average of points 7–9 for each sensor. The baselines are stored in the variables baseline FPOL, baseline ECEL and baseline PECH. The old values for the baseline (from the previous cycle) are not discarded but are instead saved in the variables prevbaseline FPOL, prevbaselineECEL and prevbaselinePECH. If the newly calculated baseline is more than 1000 Hz different than the previous baseline the data is assumed to be invalid and it is not used. Instead the previous baseline is use for that cycle. It is assumed that a baseline change of 1000 Hz is too large to be caused by real data.

POINTS 16–27—In this range the FPOL data is examined for concentrator peaks. A peak is identified as a sequence of three consecutive points for which the middle point is greater than the first and last. A peak is considered to be a positive if its height measured from the baseline exceeds a predetermined threshold value. For absolute reliability, the threshold is typically set at 150 Hz. The presence of the positive is indicated by setting the variable FPOLpeak % equal to the point where the peak was found. The height of the peak is stored in heightFPOL. Positive peaks are tested as described below.

POINTS 19–24—In this range the ECEL data is examined for concentrator peaks. A peak is identified as a sequence of three consecutive points for which the middle point is greater than the first and last. A peak is considered to be a positive if its height measured from the baseline exceeds a predetermined threshold value. For absolute reliability, the threshold is typically set at 150 Hz. The presence of the positive is indicated by setting the variable ECELpeak % equal to the point where the peak was found. The height of the peak is stored in heightECEL. Positive peaks are tested as described below.

POINTS 35–55—At every point in this range the average of the last 5 points at each sensor is calculated. The values corrected for the appropriate baseline are stored in the variables testvec(FPOL %), testvec(PECH %) and testvec(ECEL %). The ambient FPOL data is examined for baseline changes. A change in the baseline is determined by comparison of the average of the 5 most recent points with the baseline average previously determined for points 1–5. A significant change is one that is both 3 standard deviations above the baseline and also 150 Hz above the baseline. If there is a positive baseline change. The variable FPOLamb % will be set to the value of the point where the change was detected. If no change has been detected FPOLamb % will be equal to zero. As soon as a positive change has been detected the routine DOAmbNerveTest is called. In this routine the variables testvec(FPOL %), testvec(PECH %), testvec(ECEL %), coef(FPOL %), coef(PECH %), coef(ECEL %) and constant are used in the pattern recognition algorithm. Once a baseline change has been detected the pattern recognition test will be done every time until point 55.

Although the present invention has been described relative to specific exemplary embodiments thereof, it will be understood by those skilled in the art that variations and modifications can be effected in these exemplary embodiments without departing from the scope and spirit of the invention.

TABLE 2

Training Set for Nerve Agent Classification in Preconcentrator Sampling Mode

| TEST VAPOR | CONC mg/m3 | FREQUENCY SHIFT (Hz) | | |
|---|---|---|---|---|
| | | FPOL | ECEL | PECH |
| Class 1 | | | | |
| 1 DMMP, MED RH | .1 | 2259 | 86 | 431 |
| 2 DMMP, MED RH | .1 | 2251 | 97 | 442 |
| 3 DMMP, MED RH | .1 | 2276 | 112 | 438 |
| 4 DMMP, MED RH | .1 | 2397 | 70 | 227 |
| 5 DMMP, MED RH | .1 | 2290 | 85 | 206 |
| 6 DMMP, MED RH | .1 | 2171 | 119 | 0 |
| 7 DMMP, MED RH | .1 | 2192 | 120 | 346 |
| 8 DMMP, MED RH | .1 | 2388 | 128 | 315 |
| 9 DMMP, MED RH | .1 | 2328 | 129 | 306 |
| 10 DMMP, MED RH | .1 | 1633 | 68 | 246 |
| 11 DMMP, MED RH | .1 | 1620 | 56 | 244 |
| 12 DMMP, HIGH RH | .1 | 2551 | 165 | 1008 |
| 13 DMMP, HIGH RH | .1 | 2535 | 204 | 1018 |
| 14 DMMP, HIGH RH | .1 | 2544 | 219 | 1016 |
| 15 DMMP, HIGH RH | 1 | 29041 | 2660 | 16392 |
| 16 DMMP, HIGH RH | 1 | 28480 | 3339 | 16595 |
| 17 DMMP, DRY | .12 | 2294 | 0 | 793 |
| 18 DMMP, DRY | .12 | 2309 | 0 | 798 |
| 19 DMMP, DRY | .12 | 2642 | 0 | 890 |
| 20 DMMP, LOW RH | 1.12 | 13329 | 995 | 7577 |
| 21 DMMP, MED RH | 1.12 | 13772 | 1017 | 6356 |
| 22 DMMP, MED RH | 1.12 | 13660 | 1079 | 6359 |
| 23 DMMP, MED RH | 11.5 | 50248 | 12853 | 37194 |
| 24 DMMP, MED RH | 11.5 | 51429 | 12862 | 36339 |
| 25 DMMP, MED RH | 11.5 | 51285 | 13730 | 34957 |
| 26 DMMP, HIGH RH | .12 | 2067 | 265 | 686 |
| 27 DMMP, HIGH RH | .12 | 2006 | 210 | 674 |
| 28 DMMP, HIGH RH | 1.12 | 12066 | 1311 | 4399 |
| 29 DMMP, HIGH RH | 1.12 | 13025 | 1459 | 4675 |
| 30 DMMP, HIGH RH | 1.12 | 12959 | 1659 | 4681 |
| 31 DMMP, HIGH RH | 11.5 | 46876 | 19172 | 32295 |
| 32 DMMP, HIGH RH | 11.5 | 45985 | 19382 | 32150 |
| 33 DMMP, DRY | 11.5 | 49618 | 9121 | 30531 |
| 34 DMMP, DRY | 11.5 | 51007 | 8678 | 31414 |
| 35 DMMP, DRY | 11.5 | 49984 | 7919 | 41443 |
| 36 DMMP, MED RH | .12 | 2448 | 302 | 861 |
| 37 DMMP, MED RH | .12 | 2468 | 269 | 910 |
| 38 VX, LOW RH | .01 | 338 | 0 | 95 |
| 39 VX, LOW RH | .01 | 395 | 58 | 94 |
| 40 VX, LOW RH | .01 | 384 | 53 | 100 |
| 41 VX, MED RH | .01 | 380 | 74 | 114 |
| 42 VX, MED RH | .01 | 404 | 57 | 0 |
| 43 VX, HI RH | .01 | 814 | 67 | 264 |
| 44 VX, HI RH | .01 | 828 | 122 | 257 |
| 45 VX, HI RH | .01 | 827 | 84 | 252 |
| 46 VX, MED RH | .05 | 3351 | 182 | 691 |
| 47 VX, MED RH | .05 | 3319 | 223 | 687 |
| 48 VX, LOW RH | .5 | 9296 | 215 | 1230 |
| 49 VX, LOW RH | .5 | 9447 | 212 | 1183 |
| 50 VX, LOW RH | .5 | 9624 | 231 | 1226 |
| 51 VX, MED RH | .5 | 9699 | 296 | 1211 |
| 52 VX, MED RH | .5 | 9761 | 290 | 1298 |
| 53 VX, HI RH | .5 | 9596 | 603 | 1606 |
| 54 VX, HI RH | .5 | 9582 | 531 | 1509 |
| 55 VX, HI RH | .5 | 9499 | 573 | 1477 |
| 56 GD, LOW RH | .01 | 121 | 0 | 0 |
| 57 GD, LOW RH | .01 | 126 | 0 | 0 |
| 58 GD, LOW RH | .01 | 87 | 0 | 0 |
| 59 GD, HIGH RH | .5 | 7189 | 0 | 1069 |
| 60 GD, HIGH RH | .5 | 7075 | 0 | 1062 |
| 61 GD, HIGH RH | .5 | 6883 | 0 | 1044 |
| 62 GD, MED RH | .01 | 134 | 0 | 0 |
| 63 GD, MED RH | .01 | 171 | 0 | 0 |
| 64 GD, MED RH | .01 | 62 | 0 | 0 |
| 65 GD, MED RH | .01 | 170 | 0 | 0 |
| 66 GD, HIGH RH | .01 | 228 | 104 | 147 |
| 67 GD, HIGH RH | .01 | 96 | 0 | 0 |
| 68 GD, HIGH RH | .01 | 228 | 105 | 141 |
| 69 GD, HIGHRH | .01 | 207 | 112 | 159 |
| 70 GD, LOW RH | .05 | 802 | 0 | 86 |
| 71 GD, LOW RH | .05 | 755 | 0 | 99 |
| 72 GD, MED RH | .05 | 833 | 0 | 115 |
| 73 GD, MED RH | .05 | 847 | 0 | 116 |
| 74 GD, MED RH | .05 | 819 | 0 | 119 |
| 75 GD, HIGH RH | .05 | 1018 | 0 | 0 |
| 76 GD, HIGH RH | .05 | 1061 | 0 | 0 |
| 77 GD, LOW RH | 5 | 33687 | 430 | 5071 |
| 78 GD, LOW RH | 5 | 35916 | 488 | 5335 |
| 79 GD, LOW RH | 5 | 37222 | 467 | 5675 |
| 80 GD, MED RH | 5 | 40563 | 632 | 8027 |
| 81 GD, MED RH | 5 | 41109 | 679 | 8525 |
| 82 GD, HIGH RH | 5 | 43826 | 1320 | 12386 |
| 83 GD, HIGH RH | 5 | 45611 | 1311 | 11137 |
| 84 GD, HIGH RH | 5 | 46747 | 1189 | 13361 |
| 85 GD, LOW RH | .5 | 5643 | 0 | 530 |
| 86 GD, LOW RH | .5 | 5918 | 0 | 560 |
| 87 GD, LOW RH | .5 | 5754 | 0 | 556 |
| 88 GD, MED RH | .5 | 6478 | 129 | 749 |
| 89 GD, MED RH | .5 | 6520 | 130 | 753 |
| 90 DCE/GD, MED RH | 50/0.5 | 2182 | 0 | 0 |
| 91 DCE/GD, MED RH | 50/0.5 | 2154 | 0 | 0 |
| 92 DCE/GD, MED RH | 50/0.5 | 2212 | 0 | 0 |
| 93 IPA/GD, MED RH | 50/0.5 | 657 | 0 | 0 |
| 94 IPA/GD, MED RH | 50/0.5 | 652 | 50 | 0 |
| 95 GAS/GD, MED RH | 50/0.5 | 3760 | 127 | 461 |
| 96 GAS/GD, MED RH | 50/0.5 | 3745 | 0 | 459 |
| 97 GAS/GD, MED RH | 50/0.5 | 3683 | 114 | 469 |
| 98 DIESEL/ GD, MED RH | 50/0.5 | 3933 | 471 | 1665 |
| 99 DIESEL/ GD, MED RH | 50/0.5 | 3862 | 383 | 1680 |
| 100 JP4/GD, MED RH | 50/0.5 | 4540 | 197 | 528 |
| 101 JP4/GD, MED RH | 50/0.5 | 4569 | 192 | 534 |

TABLE 2-continued

Training Set for Nerve Agent Classification in Preconcentrator Sampling Mode

| TEST VAPOR | CONC mg/m3 | FPOL | ECEL | PECH |
|---|---|---|---|---|
| 102 JP4/GD, MED RH Class 2 | 50/0.5 | 4358 | 192 | 527 |
| 103 HD, LOW RH | 2 | 587 | 1124 | 6036 |
| 104 HD, LOW RH | 2 | 538 | 1376 | 6185 |
| 105 HD, MED RH | 2 | 1273 | 2278 | 13412 |
| 106 HD, MED RH | 2 | 1172 | 2205 | 13793 |
| 107 HD, HIGH RH | 2 | 2181 | 4392 | 26758 |
| 108 HD, HIGH RH | 2 | 2152 | 4101 | 26641 |
| 109 HD, HIGH RH | 2 | 2248 | 5664 | 27031 |
| 110 HD, LOW RH | 10 | 5741 | 34169 | 111991 |
| 111 HD, LOW RH | 10 | 5655 | 37337 | 113420 |
| 112 HD, MED RH | 10 | 6035 | 41341 | 113042 |
| 113 HD, MED RH | 10 | 6128 | 39054 | 113598 |
| 114 HD, MED RH | 10 | 6204 | 38543 | 112376 |
| 115 HD, HIGH RH | 10 | 6335 | 34924 | 113123 |
| 116 HD, HIGH RH | 10 | 6119 | 35034 | 111947 |
| 117 HD, LOW RH | .5 | 358 | 534 | 3325 |
| 118 HD, LOW RH | .5 | 365 | 564 | 3553 |
| 119 HD, LOW RH | .5 | 361 | 603 | 3687 |
| 120 HD, MED RH | .5 | 433 | 754 | 4165 |
| 121 HD, MED RH | .5 | 422 | 762 | 4273 |
| 122 HD, MED RH | .5 | 414 | 813 | 4439 |
| 123 HD, MED RH | .05 | 57 | 0 | 0 |
| 124 HD, MED RH | .05 | 89 | 60 | 218 |
| 125 HD, MED RH | .05 | 63 | 71 | 228 |
| 126 HD, HIGH RH | .05 | 102 | 72 | 366 |
| 127 HD, HIGH RH | .05 | 197 | 130 | 397 |
| 128 HD, HIGH RH | .05 | 165 | 95 | 353 |
| 129 HD, HIGH RH | .05 | 116 | 0 | 353 |
| 130 HD, HIGH RH | .05 | 174 | 0 | 362 |
| 131 HD, HIGH RH | .05 | 88 | 0 | 0 |
| 132 HD, HIGH RH | .05 | 84 | 0 | 0 |
| 133 AIR, LOW RH | 3 | 103 | 158 | 128 |
| 134 AIR, HIGH RH | 2 | 54 | 54 | 126 |
| 135 AIR, HIGH RH | .5 | 114 | 168 | 81 |
| 136 AIR, HIGH RH | .5 | 101 | 162 | 59 |
| 137 AIR, HIGH RH | .5 | 89 | 133 | 61 |
| 138 AIR, HIGH RH | .5 | 74 | 75 | 78 |
| 139 TOLUENE, MED RH | 51.8 | 1219 | 1037 | 3083 |
| 140 TOLUENE, MED RH | 51.8 | 1190 | 1021 | 2962 |
| 141 TOLUENE, MED RH | 51.8 | 1208 | 1034 | 2957 |
| 142 DCP, MED RH | 42 | 15372 | 34262 | 51318 |
| 143 DCP, MED RH | 42 | 15283 | 36266 | 48397 |
| 144 DCP, MED RH | 3.6 | 1755 | 2360 | 6971 |
| 145 DCP, MED RH | 3.6 | 1803 | 2390 | 7153 |
| 146 DCP, MED RH | 3.6 | 1862 | 2595 | 7306 |
| 147 DCP, DRY | 3.6 | 1536 | 2512 | 7638 |
| 148 DCP, DRY | 3.6 | 1533 | 2697 | 7617 |
| 149 DCP, DRY | 3.6 | 1528 | 2616 | 7611 |
| 150 DCP, med RH | 3 | 1055 | 1029 | 3759 |
| 151 DCP, med RH | 3 | 1077 | 977 | 3991 |
| 152 DCP, HIGH RH | 3 | 1182 | 1062 | 4859 |
| 153 DCP, HIGH RH | 3 | 1155 | 1050 | 4873 |
| 154 DCP, HIGH RH | 3 | 209 | 207 | 0 |
| 155 DCP, low RH | 3 | 908 | 1026 | 2858 |
| 156 DCP, low RH | 3 | 895 | 934 | 2734 |
| 157 DCP, low RH | 3 | 873 | 1154 | 3011 |
| 158 DCP, LOW RH | 35 | 15413 | 31812 | 109789 |
| 159 DCP, LOW RH | 35 | 15295 | 43094 | 108313 |
| 160 DCP, MED RH | 35 | 17403 | 43090 | 115811 |
| 161 DCP, MED RH | 35 | 16283 | 42953 | 112759 |
| 162 DCP, MED RH | 35 | 17006 | 43422 | 111956 |
| 163 DCP, HIGH RH | 35 | 16801 | 45019 | 105019 |
| 164 DCP, HIGH RH | 35 | 16888 | 38231 | 102964 |
| 165 DCE, LOW RH | 50 | 93 | 342 | 476 |
| 166 DCE, LOW RH | 50 | 171 | 319 | 451 |
| 167 DCE, LOW RH | 50 | 159 | 320 | 450 |
| 168 DCE, MED RH | 50 | 179 | 279 | 425 |
| 169 DCE, MED RH | 50 | 181 | 263 | 416 |
| 170 DCE, MED RH | 50 | 188 | 255 | 412 |
| 171 GAS, MED RH | so | 67 | 77 | 142 |
| 172 GAS, MED RH | 50 | 63 | 0 | 133 |
| 173 GAS, LOW RH | so | 53 | 0 | 93 |
| 174 DIESEL, LOW RH | 50 | 310 | 0 | 1058 |
| 175 DIESEL, LOW RH | so | 307 | 229 | 1118 |
| 176 DIESEL, LOW RH | 50 | 328 | 240 | 1090 |
| 177 DIESEL, MED RH | 50 | 405 | 385 | 1135 |
| 178 DIESEL, MED RH | 50 | 436 | 402 | 1233 |
| 179 DIESEL, MED RH | 50 | 422 | 400 | 1220 |
| 180 CIGARETTE, VARIES | | 564 | 228 | 704 |
| 181 CIGARETTE, VARIES | | 494 | 244 | 694 |
| 182 GAS EXH, VARIES | | 417 | 173 | 578 |
| 183 GAS EXH, VARIES | | 413 | 161 | 586 |
| 184 GAS EXH, VARIES | | 387 | 92 | 596 |
| 185 JET EXH, VARIES | | 1570 | 297 | 2377 |
| 186 JET EXH, VARIES | | 1182 | 92 | 1842 |
| 187 JET EXH, VARIES | | 1136 | 432 | 1725 |
| 188 DIESEL EXH, VARIES | | 231 | 90 | 439 |
| 189 DIESEL EXH, VARIES | | 174 | 94 | 0 |
| 190 DIESEL EXH, VARIES | | 360 | 98 | 609 |
| 191 DIESEL EXH, VARIES | | 232 | 102 | 0 |
| 192 DIESEL/HD, MED RH | 50/2 | 2200 | 5797 | 29713 |
| 193 DIESEL/HD, MED RH | 50/2 | 2225 | 6991 | 29750 |
| 194 JP4/HD, MED RH | 50/2 | 1870 | 0 | 25726 |
| 195 JP4/HD, MED RH | 50/2 | 1855 | 4875 | 25912 |
| 196 JP4/HD, MED RH | 50/2 | 1881 | 6656 | 25433 |
| 197 DCE/HD, MED RH | 50/2 | 1513 | 964 | 3557 |
| 198 DCE/HD, MED RH | 50/2 | 522 | 972 | 3639 |
| 199 DCE/HD, MED RH | 50/2 | 502 | 987 | 3704 |
| 200 DCE/HD, MED RH | 50/2 | 532 | 1056 | 3697 |
| 201 DCE/HD, MED RH | 50/2 | 500 | 1065 | 3804 |
| 202 IPA/HD, MED RH | 50/2 | 1562 | 2311 | 17271 |
| 203 IPA/HD, MED RH | 50/2 | 1474 | 3570 | 17894 |
| 204 GAS/HD, MED RH | 50/2 | 1584 | 4187 | 20480 |
| 205 GAS/HD, MED RH | 50/2 | 1505 | 3774 | 19493 |
| 206 GAS/HD, MED RH | 50/2 | 1522 | 4673 | 19850 |

TABLE 3

Training Set for Nerve Agent Classification in Direct Sampling Mode

| TEST VAPOR | CONC mg/m3 | FPOL | ECEL | PECH |
|---|---|---|---|---|
| Class 1 | | | | |
| 1 DMMP, DRY | .1 | 61 | 20 | 15 |
| 2 DMMP, LOW RH | .1 | 64 | 30 | -32 |
| 3 DMMP, LOW RH | 11 | 1771 | 82 | 1002 |
| 4 DMMP, LOW AN | 1 | 181 | -15 | 183 |
| 5 DMMP, DRY | 1 | 189 | 69 | 215 |
| 6 DMMP, MED RH | .1 | 66 | -102 | 49 |
| 7 DMMP, MED RH | 1 | 206 | -62 | 178 |
| 8 DMMP, MED RH | 11 | 1809 | 104 | 1554 |
| 9 DMMP, HIGH RH | 1 | 103 | -388 | 162 |
| 10 DMMP, HIGH RH | 11 | -70 | 14 | 4 |

TABLE 3-continued

Training Set for Nerve Agent Classification in Direct Sampling Mode

| TEST VAPOR | CONC mg/m3 | FPOL | ECEL | PECH |
|---|---|---|---|---|
| 11 DMMP, DRY | 11 | 8 | 28 | 82 |
| 12 DMMP, HIGH RH | 1 | 116 | -7 | 15 |
| 13 DMMP, HIGH RH | 10 | 3230 | 132 | 646 |
| 14 GD, LOW RH | 5 | 445 | 33 | 28 |
| 15 GD, MED RH | 5 | 934 | -15 | 3 |
| 16 GD, HIGH RH | 5 | 1146 | -70 | 20 |
| 17 VX, LOW RH | .5 | 107 | 14 | -20 |
| 18 DMMP, MED RH | .1 | 53 | -19 | -56 |
| 19 VX, MED RH | .5 | 99 | -15 | -45 |
| 20 GD, MED RH | .5 | 70 | -23 | -39 |
| 21 DMMP, DRY | .1 | 80 | 18 | 7 |
| 22 DMMP, LOW RH | 11 | 6309 | 158 | 1567 |
| 23 DMMP, LOW RH | 1 | 594 | 15 | 223 |
| 24 DMMP, DRY | 1 | 573 | 105 | 280 |
| 25 DMMP, MED RH | 1 | 632 | -46 | 211 |
| 26 DMMP, MED RH | 11 | 6420 | 399 | 2199 |
| 27 DMMP, HIGH RH | 1 | 543 | -413 | 193 |
| 28 DMMP, HIGH RH | 11 | 2341 | 39 | 1447 |
| 29 DMMP, DRY | 11 | 1799 | 126 | 1516 |
| 30 DMMP, HIGH RH | 1 | 427 | -104 | 18 |
| 31 DMMP, HIGH RH | 10 | 6982 | 162 | 903 |
| 32 GD, LOW RH | 5 | 1113 | 24 | 75 |
| 33 GD, MED RH | 5 | 1695 | -12 | 66 |
| 34 GD, HIGH RH | 5 | 2038 | -101 | 67 |
| 35 VX, LOW RH | .5 | 202 | 26 | 18 |
| 36 VX, MED RH | .5 | 200 | -10 | -38 |
| 37 GD, MED RH | .5 | 97 | -28 | -35 |
| 38 DMMP, LOW RH | 11 | 8952 | 211 | 1607 |
| 39 DMMP, LOW RH | 1 | 882 | 30 | 207 |
| 40 DMMP, DRY | 1 | 844 | 122 | 268 |
| 41 DMMP, MED RH | 1 | 928 | -42 | 202 |
| 42 DMMP, MED RH | 11 | 9311 | 575 | 2179 |
| 43 DMMP, HIGH RH | 1 | 849 | -437 | 190 |
| 44 DMMP, HIGH RH | 11 | 6783 | 370 | 1672 |
| 45 DMMP, DRY | 11 | 5547 | 285 | 2170 |
| 46 DMMP, HIGH RH | 1 | 993 | -126 | 39 |
| 47 DMMP, HIGH RH | 10 | 8919 | 193 | 1295 |
| 48 GD, LOW RH | 5 | 1456 | 26 | 97 |
| 49 GD, MED RH | 5 | 2159 | -9 | 102 |
| 50 GD, HIGH RH | 5 | 2550 | -118 | 96 |
| 51 DMMP, HIGH RH | 11 | 9292 | 594 | 1621 |
| 52 DMMP, DRY | 11 | 7869 | 399 | 2184 |
| Class 2 | | | | |
| 53 TOLUENE, MED RH | 52 | 3 | -21 | 261 |
| 54 DCE, MED RH | 58 | -11 | 21 | 78 |
| 55 TOLUENE, DRY | 500 | 150 | 11 | 646 |
| 56 ISOOCTANE, DRY | 500 | 25 | 7 | 92 |
| 57 AIR, LOW RU | | 346 | 2050 | 339 |
| 58 AIR, MED RH | | 2103 | 16489 | 793 |
| 59 AIR, HIGH RH | | 8730 | 108594 | 11400 |
| 60 DIESEL, LOW RH | 50 | -76 | 45 | 83 |
| 61 CIGARETTE SMOKE | | 469 | -343 | 526 |
| 62 GAS | | 252 | 109 | 373 |
| 63 DCP, LOW RH | 35 | 19 | 83 | 126 |
| 64 DCP, HIGH RH | 35 | 73 | -64 | 116 |
| 65 DCP, MED RD | 42 | 273 | 241 | 242 |
| 66 DCP, MED RH | 4 | 4 | 0 | 22 |
| 67 DCP, DRY | 4 | 49 | 67 | 165 |
| 68 DCP, MED RH | 35 | -87 | 45 | 96 |
| 69 HD, HIGH RH | 2 | -195 | -109 | 77 |
| 70 HD, LOW RH | 10 | -44 | 111 | 237 |
| 71 HD, HIGH RH | 10 | -152 | 243 | 424 |
| 72 HD, LOW RH | .5 | 8 | 87 | -11 |
| 73 HD, MED RH | 2 | -31 | 3 | 88 |
| 74 HD, MED RH | 10 | -2 | 143 | 476 |
| 75 IPA/HD, MED RH | 50/2 | 3 | 28 | 78 |
| 76 GAS/HD, MED RH | 50/2 | -97 | 11 | 82 |
| 77 JP4/HD, MED RH | 50/2 | -74 | 32 | 92 |
| 78 DIESEL/HD, MED RH | 50/2 | -66 | 33 | 164 |
| 79 TOLUENE, MED RH | 52 | -11 | -96 | 345 |
| 80 DCE, MED RH | 58 | -57 | -72 | 121 |
| 81 TOLUENE, MED RH | 500 | 197 | 106 | 591 |
| 82 ISOOCTANE, DRY | 500 | 46 | 20 | 104 |
| 83 AIR, LOW RH | | 422 | 2399 | 344 |
| 84 AIR, MED RH | | 3401 | 23223 | 739 |
| 85 AIR, HIGH RH | | 9934 | 117698 | 13950 |
| 86 DIESEL, LOW RH | 50 | -80 | 60 | 92 |
| 87 CIGARETTE SMOKE | | 546 | 483 | 524 |
| 88 GAS EXKAUST | | 418 | 131 | 574 |
| 89 DCP, LOW RH | 35 | 26 | 72 | 217 |
| 90 DCP, HIGH RH | 35 | 78 | -61 | 194 |
| 91 DCP, MED RH | 42 | 437 | 438 | 440 |
| 92 DCP, MED RH | 4 | -25 | -69 | 127 |
| 93 DCP, DRY | 4 | 65 | 98 | 178 |
| 94 DCP, MED RH | 35 | -65 | 83 | 162 |
| 95 HD, HIGH RH | 2 | -177 | -93 | 127 |
| 96 HD, LOW RH | 10 | -6 | 189 | 644 |
| 97 HD, HIGH RH | 10 | -102 | -174 | 807 |
| 98 HD, LOW RH | .5 | 8 | 106 | 10 |
| 99 HD, MED RH | 2 | -27 | 13 | 133 |
| 100 HD, MED RH | 10 | 33 | 285 | 806 |
| 101 IPA/HD, MED RH | 50/2 | 11 | 30 | 118 |
| 102 JP4/HD, MED RH | 50/2 | -65 | 58 | 156 |
| 103 TOLUENE, MED RH | 52 | -10 | -111 | 354 |
| 104 DCE, MED RH | 58 | -58 | -98 | 125 |
| 105 TOLUENE, DRY | 500 | 197 | 131 | 559 |
| 106 ISOOCTANE, DRY | 500 | 51 | 23 | 94 |
| 107 AIR, LOW RH | | 444 | 2405 | 320 |
| 108 AIR, MED RH | | 3611 | 23898 | 934 |
| 109 AIR, HIGH RH | | 9993 | 118828 | 14337 |
| 110 DIESEL, LOW RH | 50 | -86 | 68 | 104 |
| 111 CIGARETTE SMOKE | | 515 | -558 | 468 |
| 112 GAS EXHAUST | | 449 | 143 | 606 |
| 113 DCP, LOW RH | 35 | 53 | 54 | 273 |
| 114 DCP, HIGH RH | 35 | 62 | -67 | 224 |
| 115 DCP, MED RH | 4 | -16 | -61 | 145 |
| 116 DCP, DRY | 4 | 69 | 111 | 176 |
| 117 HD, LOW RH | 10 | 4 | 199 | 814 |
| 118 HD, HIGH RH | 10 | -81 | -148 | 937 |
| 119 HD, LOW RH | .5 | 14 | 124 | 45 |
| 120 HD, MED RH | 10 | 49 | 426 | 942 |
| 121 TOLUENE, MED RH | 52 | -13 | -125 | 354 |
| 122 DCE, MED RH | 58 | -64 | -108 | 117 |
| 123 DIESEL, LOW RH | 50 | -89 | 73 | 103 |
| 124 DCP, MED RH | 4 | -14 | -59 | 144 |
| 125 HD, LOW RH | .5 | 26 | 136 | 63 |

TABLE 4

Training Set for Blister Agent Classification in Preconcentrator Sampling Mode[a]

| TEST VAPOR | CONC mg/m3 | FPOL | ECEL | PECH |
|---|---|---|---|---|
| Class 1 | | | | |
| 1 HD, LOW RH | 2 | 592 | 1121 | 6021 |
| 2 HD, LOW RH | 2 | 587 | 1124 | 6036 |
| 3 HD, LOW RH | 2 | 534 | 1104 | 5969 |
| 4 HD, LOW RH | 2 | 538 | 1376 | 6185 |
| 5 HD, LOW RH | 2 | 551 | 1378 | 6320 |
| 6 HD, MED RH | 2 | 1273 | 2278 | 13412 |
| 7 HD, MED RH | 2 | 1216 | 2217 | 13900 |

TABLE 4-continued

Training Set for Blister Agent Classification in Preconcentrator Sampling Mode[a]

| TEST VAPOR | CONC mg/m3 | FREQUENCY SHIFTS (Hz) | | |
|---|---|---|---|---|
| | | FPOL | ECEL | PECH |
| 8 HD, MED RH | 2 | 1172 | 2205 | 13793 |
| 9 HD, MED RH | 2 | 1248 | 2788 | 14485 |
| 10 HD, HIGH RH | 2 | 2181 | 4392 | 26758 |
| 11 HD, HIGH RH | 2 | 2197 | 4208 | 26692 |
| 12 HD, HIGH RH | 2 | 2152 | 4101 | 26641 |
| 13 HD, HIGH RH | 2 | 2206 | 6166 | 27023 |
| 14 HD, HIGH RH | 2 | 2248 | 5664 | 27031 |
| 15 HD, LOW RH | 10 | 5670 | 35377 | 111961 |
| 16 HD, LOW RH | 10 | 5741 | 34169 | 111991 |
| 17 HD, LOW RH | 10 | 5753 | 39015 | 113262 |
| 18 HD, LOW RH | 10 | 5655 | 373377 | 113420 |
| 19 HD, LOW RH | 10 | 5663 | 36349 | 112928 |
| 20 HD, MED RH | 10 | 6035 | 41341 | 113042 |
| 21 HD, MED RH | 10 | 6306 | 39658 | 113291 |
| 22 HD, MED RH | 10 | 6128 | 39054 | 113598 |
| 23 HD, MED RH | 10 | 6290 | 37812 | 112739 |
| 24 HD, MED RH | 10 | 6204 | 38543 | 112376 |
| 25 HD, HIGH RH | 10 | 6380 | 35588 | 112732 |
| 26 HD, HIGH RH | 10 | 6335 | 34924 | 113123 |
| 27 HD, HIGH RH | 10 | 6227 | 33195 | 112595 |
| 28 HD, HIGH RH | 10 | 6119 | 35034 | 111947 |
| 29 HD, HIGH RH | 10 | 6218 | 35150 | 112780 |
| 30 HD, LOW RH | .5 | 358 | 534 | 3325 |
| 31 HD, LOW RH | .5 | 343 | 545 | 3499 |
| 32 HD, LOW RH | .5 | 365 | 564 | 3553 |
| 33 HD, LOW RH | .5 | 358 | 641 | 3542 |
| 34 HD, LOW RH | .5 | 361 | 603 | 3687 |
| 35 HD, LOW RH | .5 | 361 | 628 | 3759 |
| 36 HD, MED RH | .5 | 433 | 784 | 4165 |
| 37 HD, MED RH | .5 | 393 | 776 | 4216 |
| 38 HD, MED RH | .5 | 422 | 762 | 4273 |
| 39 HD, MED RH | .5 | 457 | 834 | 4386 |
| 40 HD, MED RH | .5 | 414 | 813 | 4439 |
| 41 DIESEL/HD, MED RH | 50/2 | 2288 | 5868 | 29564 |
| 42 DIESEL/HD, MED RH | 50/2 | 2200 | 5797 | 29713 |
| 43 DIESEL/HD, MED RH | 50/2 | 2233 | 5856 | 29599 |
| 44 DIESEL/HD, MED RH | 50/2 | 2225 | 6991 | 29750 |
| 45 DIESEL/HD, MED RH | 50/2 | 2235 | 6931 | 30056 |
| 46 JP4/HD, MED RH | 50/2 | 1870 | 4600 | 25726 |
| 47 JP4/HD, MED RH | 50/2 | 1866 | 4803 | 26433 |
| 48 JP4/HD, MED RH | 50/2 | 1855 | 4875 | 25912 |
| 49 JP4/HD, MED RH | 50/2 | 1881 | 6922 | 28261 |
| 50 JP4/HD, MED RH | 50/2 | iwi | 6656 | 28433 |
| 51 DCE/HD, MED RH | 50/2 | 513 | 984 | 3557 |
| 52 DCE/HD, MED RH | 50/2 | 522 | 972 | 3639 |
| 53 DCE/HD, MED RH | 50/2 | 502 | 987 | 3704 |
| 54 OCE/HD, MED RH | 50/2 | 532 | 1056 | 3697 |
| 55 DCE/HD, MED RH | 50/2 | 500 | 1065 | 3804 |
| 56 IPA/HD, MED RH | 50/2 | 1500 | 2313 | 17266 |
| 57 IPA/HD, MED RH | 50/2 | 1562 | 2311 | 17271 |
| 58 IPA/HD, MED RH | 50/2 | 1604 | 2302 | 17219 |
| 59 IPA/HD, MED RH | 50/2 | 1474 | 3570 | 17894 |
| 60 IPA/HD, MED RH | 50/2 | 1488 | 3441 | 17914 |
| 61 GAS/HD, MED RH | 50/2 | 1584 | 4187 | 20480 |
| 62 GAS/HD, MED RH | 50/2 | 1525 | 3926 | 19645 |
| 63 GAS/HD, MED RH | 50/2 | 1505 | 3774 | 19493 |
| 64 GAS/HD, MED RH | 50/2 | 1522 | 5076 | 20114 |
| 65 GAS/HD, MED RH | 50/2 | 1522 | 4673 | 19850 |
| Class 2 | | | | |
| 66 DMMP, MED RH | .1 | 2259 | 86 | 431 |
| 67 DMMP, MED RH | .1 | 2275 | 105 | 423 |
| 68 DMMP, MED RH | .1 | 2251 | 97 | 442 |
| 69 DMMP, MED RH | .1 | 2193 | 106 | 414 |
| 70 DMMP, MED RH | .1 | 2276 | 112 | 438 |
| 71 DMMP, MED RH | .1 | 2346 | 63 | 230 |
| 72 DMMP, MED RH | i | 2397 | 70 | 227 |
| 73 DMMP, MED RH | .1 | 2406 | 62 | 220 |
| 74 DMMP, MED RH | .1 | 2290 | 85 | 206 |
| 75 DMMP, MED RH | .1 | 2193 | 124 | 0 |
| 76 DMMP, MED RH | .1 | 2171 | 119 | 0 |
| 77 DMMP, MED RH | .1 | 2191 | 125 | 339 |
| 78 DMMP, MED RH | .1 | 2192 | 120 | 346 |
| 79 DMMP, MED RH | .1 | 2343 | 109 | 311 |
| 80 DMMP, MED RH | .1 | 23W | 128 | 315 |
| 81 DMMP, MED RH | .1 | 2419 | 126 | 332 |
| 82 DMMP, MED RH | .1 | 2328 | 129 | 308 |
| 83 DMMP, MED RH | .1 | 2342 | 80 | 318 |
| 84 DMMP, MED RH | .1 | 1633 | 68 | 246 |
| 85 DMMP, MED RH | .1 | 1648 | 71 | 237 |
| 86 DMMP, MED RH | .1 | 1620 | 56 | 244 |
| 87 DMMP, MED RH | .1 | 1730 | 65 | 238 |
| 88 DMMP, MED RH | .1 | 2369 | 288 | 844 |
| 89 DMMP, MED RH | .1 | 2448 | 302 | 861 |
| 90 DMMP, MED RH | .1 | 2493 | 298 | 891 |
| 91 DMMP, MED RH | .1 | 2468 | 269 | 910 |
| 92 DMMP, MED RH | .1 | 2502 | 276 | 917 |
| 93 VX, LOW RH | .01 | 338 | 0 | 95 |
| 94 VX, LOW RH | .01 | 376 | 0 | 92 |
| 95 VX, LOW RH | .01 | 395 | 58 | 94 |
| 96 VX, LOW RH | .01 | 382 | 0 | 0 |
| 97 VX, LOW RH | .01 | 384 | 53 | 100 |
| 98 VX, MED RH | .01 | 348 | 67 | 61 |
| 99 VX, MED RH | .01 | 380 | 74 | 114 |
| 100 VX, MED RH | .01 | 340 | 0 | 101 |
| 101 VX, MED RH | .01 | 404 | 0 | 120 |
| 102 VX, HIGH RH | .01 | 814 | 67 | 264 |
| 103 VX, HIGH RH | .01 | 799 | 112 | 242 |
| 104 VX, HIGH RH | .01 | 828 | 122 | 257 |
| 105 VX, HIGH RH | .01 | 842 | 168 | 265 |
| 106 VX, HIGH RH | .01 | 827 | 84 | 252 |
| 107 VX, MED RH | .05 | 3302 | 169 | 731 |
| 108 VX, MED RH | .05 | 3351 | 182 | 691 |
| 109 VX, MED RH | .05 | 3352 | 156 | 663 |
| 110 VX, MED RH | .05 | 3319 | 223 | 687 |
| 111 VX, MED RH | .05 | 3320 | 159 | 698 |
| 112 VX, LOW RH | .5 | 9296 | 215 | 1230 |
| 113 VX, LOW RH | .5 | 9222 | 198 | 1190 |
| 114 VX, LOW RH | .5 | 9447 | 212 | 1183 |
| 115 VX, LOW RH | .5 | 9676 | 253 | 1286 |
| 116 VX, LOW RH | .5 | 9624 | 231 | 1226 |
| 117 VX, MED RH | .5 | 9755 | 312 | 1276 |
| 118 VX, MED RH | .5 | 9699 | 296 | 1211 |
| 119 VX, MED RH | .5 | 9769 | 307 | 1193 |
| 120 VX, MED RH | .5 | 9761 | 290 | 1298 |
| 121 VX, MED RH | .5 | 9710 | 337 | 1270 |
| 122 VX, HIGH RH | .5 | 9596 | 603 | 1606 |
| 123 VX, HIGH RH | .5 | 9625 | 577 | 1544 |
| 124 VX, HIGH RH | .5 | 9582 | 531 | 1509 |
| 125 VX, HIGH RH | .5 | 9593 | 616 | 1538 |
| 126 VX, HIGH RH | .5 | 9499 | 573 | 1477 |
| 127 AIR HIGH RH | | 54 | 54 | 126 |
| 128 AIR HIGH RH | | 96 | 142 | 72 |
| 129 AIR HIGH RH | | 114 | 168 | 81 |
| 130 AIR HIGH RH | | 96 | 74 | 78 |
| 131 CIGARETTE SMOKE | | 114 | 228 | 704 |
| 132 CIGARETTE SMOKE | | 492 | 223 | 737 |
| 133 CIGARETTE SMOKE | | 494 | 244 | 694 |
| 134 CIGARETTE SMOKE | | 517 | 759 | 715 |
| 135 GAS EXHAUST | | 417 | 173 | 578 |
| 136 GAS EXHAUST | | 353 | 142 | 577 |
| 137 GAS EXHAUST | | 413 | 161 | 586 |
| 138 GAS EXHAUST | | 467 | 172 | 608 |
| 139 GAS EXHAUST | | 357 | 92 | 596 |
| 140 JET EXHAUST | | 1306 | 236 | 1863 |
| 141 JET EXHAUST | | 1570 | 297 | 2377 |
| 142 JET EXHAUST | | 1257 | 405 | 1956 |

TABLE 4-continued

Training Set for Blister Agent Classification in Preconcentrator Sampling Mode[a]

| TEST VAPOR | CONC mg/m3 | FPOL | ECEL | PECH |
|---|---|---|---|---|
| 143 JET EXHAUST | | 1182 | 461 | 1842 |
| 144 JET EXHAUST | | 1083 | 463 | 1677 |
| 145 JET EXHAUST | | 1136 | 432 | 1725 |
| 146 JET EXHAUST | | 1103 | 440 | 1819 |
| 147 DIESEL EXHAUST | | 231 | 90 | 439 |
| 148 DIESEL EXHAUST | | 272 | 117 | 602 |
| 149 DIESEL EXHAUST | | 348 | 113 | 607 |
| 150 DIESEL EXHAUST | | 360 | 98 | 609 |
| 151 DIESEL EXHAUST | | 328 | 104 | 615 |

[a]Training done without DCP or 0.05 mg/m$^3$ HD in the training set

TABLE 5

Training Set for Blister Agent Classification in Direct Sampling Mode

| TEST VAPOR | CONC mg/m3 | FPOL | ECEL | PECH |
|---|---|---|---|---|
| Class 1 | | | | |
| 1 HD, HIGH RH | 2 | −195 | −109 | 77 |
| 2 HD, LOW RH | 10 | −44 | 111 | 237 |
| 3 HD, HIGH RH | 10 | −152 | −243 | 424 |
| 4 HD, LOW RH | .5 | 8 | 106 | 10 |
| 5 HD, MED RH | 2 | −31 | 3 | 88 |
| 6 HD, MED RH | 10 | −2 | 143 | 476 |
| 7 IPA/HD, MED RH | 50/2 | 3 | 28 | 78 |
| 8 GAS/HD, MED RH | 50/2 | −97 | 11 | 82 |
| 9 JP-4/HD, MED RH | 50/2 | −74 | 32 | 92 |
| 10 DIESEL/HD, MED RH | 50/2 | −66 | 33 | 164 |
| 11 HD, HIGH RH | 2 | −177 | −93 | 127 |
| 12 HD, LOW RH | 10 | −6 | 189 | 644 |
| 13 HD, HIGH RH | 10 | −102 | −174 | 807 |
| 14 HD, LOW RH | .5 | 11 | 124 | 45 |
| 15 HD, MED RH | 2 | −27 | 13 | 133 |
| 16 HD, MED RH | 10 | 33 | 285 | 806 |
| 17 IP/HD, MED RH | 50/2 | 11 | 30 | 118 |
| 18 JP4/HD, MED RH | 50/2 | −65 | 58 | 156 |
| 19 HD, LOW RH | 10 | 4 | 199 | 814 |
| 20 HD, HIGH RH | 10 | −81 | −148 | 937 |
| 21 HD, LOW RH | .5 | 26 | 136 | 63 |
| 22 HD, MED RH | 10 | 49 | 426 | 942 |
| Class 2 | | | | |
| 23 DMMP, DRY | .1 | 61 | 20 | 15 |
| 24 DMMP, LOW RH | .1 | 64 | −30 | −32 |
| 25 DMMP, LOW RH | 11 | 1771 | 82 | 1002 |
| 26 DMMP, LOW RH | 1 | 181 | −15 | 183 |
| 27 DMMP, DRY | 1 | 189 | 69 | 215 |
| 28 DMMP, MED RH | .1 | 66 | −102 | 49 |
| 29 DMMP, MED RH | 1 | 206 | −62 | 178 |
| 30 DMMP, MED RH | 11 | 1809 | 104 | 1554 |
| 31 DMMP, HIGH RH | 1 | 103 | −388 | 162 |
| 32 DMMP, HIGH RH | 11 | 2341 | 39 | 1447 |
| 33 DMMP, DRY | 11 | 1799 | 126 | 1516 |
| 34 DMMP, HIGH RH | 1 | 116 | −7 | 15 |
| 35 DMMP, HIGH RH | 10 | 3230 | 132 | 646 |
| 36 GD, LOW RH | 5 | 445 | 33 | 28 |
| 37 GD, MED RH | 5 | 934 | −15 | 3 |
| 38 GD, HIGH RH | 5 | 1146 | −70 | 20 |
| 39 VX, LOW RH | .5 | 107 | 14 | −20 |
| 40 DMMP, MED RH | .1 | 53 | 19 | −56 |
| 41 VX, MED RH | .5 | 99 | −15 | −45 |
| 42 GD, MED RH | .5 | 70 | −23 | −39 |
| 43 TOLUENE, DRY | 500 | 150 | 11 | 646 |
| 44 ISOOCTANE, DRY | 500 | 25 | 7 | 92 |
| 45 AIR, LOW RH | | 346 | 2050 | 339 |
| 46 AIR, MED RH | | 2103 | 16489 | 793 |
| 47 AIR, HIGH RH | | 8730 | 108594 | 11400 |
| 48 DIESEL, LOW RH | 50 | −76 | 45 | 83 |
| 49 CIGARETTE SMOKE | | 469 | −343 | 526 |
| 50 GAS EXHAUST | | 252 | 109 | 373 |
| 51 DMMP, DRY | .1 | 80 | 18 | 7 |
| 52 DMMP, LOW RH | 11 | 6309 | 158 | 1567 |
| 53 DMMP, LOW RH | 1 | 594 | 15 | 223 |
| 54 DMMP, DRY | 1 | 573 | 105 | 280 |
| 55 DMMP, MED RH | 1 | 632 | −46 | 211 |
| 56 DMMP, MED RH | 11 | 6420 | 399 | 2199 |
| 57 DMMP, HIGH RH | 1 | 543 | −413 | 193 |
| 58 DMMP, HIGH RH | 11 | 6783 | 370 | 1672 |
| 59 DMMP, DRY | 11 | 5547 | 285 | 2170 |
| 60 DMMP, HIGH RH | 1 | 427 | −104 | 18 |
| 61 DMMP, HIGH RH | 10 | 6982 | 162 | 903 |
| 62 GD, LOW RH | 5 | 1113 | 24 | 75 |
| 63 GD, MED RH | 5 | 1695 | −12 | 66 |
| 64 GD, HIGH RH | 5 | 2038 | −101 | 67 |
| 65 VX, LOW RH | .5 | 202 | 26 | 18 |
| 66 VX, MED RH | .5 | 2038 | −10 | −38 |
| 67 GD, MED RH | .5 | 97 | −28 | −35 |
| 68 TOLUENE, MED RH | 52 | −11 | −96 | 348 |
| 69 DCE, MED RH | 58 | −57 | −72 | 121 |
| 70 TOLUENE, DRY | 500 | 197 | 106 | 591 |
| 71 ISOOCTANE, DRY | 500 | 46 | 20 | 104 |
| 72 AIR, LOW RH | | 422 | 2399 | 344 |
| 73 AIR, MED RH | | 3401 | 23223 | 739 |
| 74 AIR, HIGH RH | | 9934 | 117698 | 13950 |
| 75 DIESEL, LOW RH | 50 | −80 | 60 | 92 |
| 76 CIGARETTE SMOKE | | 546 | −483 | 524 |
| 77 GAS EXHAUST | | 418 | 131 | 574 |
| 78 DMMP, LOW RH | 11 | 8952 | 214 | 1607 |
| 79 DMMP, LOW RH | 1 | 882 | 30 | 207 |
| 80 DMMP, DRY | 1 | 844 | 122 | 268 |
| 81 DMMP, MED RH | 1 | 928 | −42 | 202 |
| 82 DMMP, MED RH | 11 | 9311 | 575 | 2179 |
| 83 DMMP, HIGH RH | 1 | 549 | 437 | 190 |
| 84 DMMP, HIGH RH | 11 | 9292 | 594 | 1621 |
| 85 DMMP, DRY | 11 | 7369 | 399 | 2184 |
| 86 DMMP, HIGH RH | 1 | 993 | −126 | 39 |
| 87 DMMP, HIGH RH | 10 | 8919 | 193 | 1295 |
| 88 GD, LOW RH | 5 | 1456 | 26 | 97 |
| 89 GD, MED RH | 5 | 2159 | −9 | 102 |
| 90 GD, HIGH RH | 5 | 2550 | −118 | 96 |
| 91 TOLUENE, MED RH | 52 | −10 | −111 | 354 |
| 92 DCE, MED RH | 58 | −58 | −88 | 125 |
| 93 TOLUENE, DRY | 500 | 197 | 131 | 559 |
| 94 ISOOCTANE, DRY | 500 | 51 | 23 | 94 |
| 95 AIR, LOW RH | | 444 | 2405 | 320 |
| 96 AIR, MED RH | | 3611 | 23898 | 934 |
| 97 AIR, HIGH RH | | 9993 | 118828 | 14337 |
| 98 DIESEL, LOW RH | 50 | −86 | 68 | 104 |
| 99 CIGARETTE SMOKE | | 515 | −558 | 468 |
| 100 GAS EXHAUST | | 449 | 143 | 606 |
| 101 TOLUENE, MED RH | 52 | −13 | −125 | 354 |
| 102 DCE, MED RH | 58 | −64 | −108 | 117 |
| 103 DIESEL, LOW RH | 50 | −89 | 73 | 103 |

[a]Training done without DCP in the training set.

TABLE 7

Prediction Set of Data Collected in Direct Sampling Mode

| | CONC | FREQUENCY SHIFTS (Hz) | | |
|---|---|---|---|---|
| TEST VAPOR | mg/m3 | FPOL | ECEL | PECH |
| 1 VX, MED RH | .05 | 74 | 23 | 2 |
| 2 VX, MED RH | .5 | 332 | 175 | 119 |
| 3 GD/HD, MED RH | .5/2 | 0 | 0 | 38 |
| 4 VX, MED RH | .5 | 594 | 80 | 159 |
| 5 VX, MED RH | .05 | 196 | 60 | 37 |
| 6 AMMONIA, MED RH | 50 | 0 | 119 | 30 |
| 7 HD, MED RH | 2 | 0 | 0 | 65 |
| 8 AMMONIA/GD, MED RH | 50/.5 | 1 | 174 | 59 |
| 9 AMMONIA/HD, MED RH | 50/2 | 0 | 150 | 55 |
| 10 DCP, MED RH | 35 | 0 | 49 | 161 |
| 11 DMMP, MED RH | 1 | 300 | 20 | 0 |
| 12 VX, MED RH | .05 | 126 | 65 | 32 |
| 13 VX, MED RH | .5 | 699 | 290 | 228 |
| 14 GD/HD, MED RH | .5/2 | 0 | 0 | 73 |
| 15 VX, MED RH | .05 | 393 | 73 | 129 |
| 16 AMMONIA, MED RH | 50 | 0 | 202 | 50 |
| 17 AMMONIA/GD, MED RH | 50/.5 | 28 | 281 | 108 |
| 18 AMMONIA/HD, MED RH | 50/2 | 0 | 241 | 99 |
| 19 DCP, MED RH | 35 | 0 | 66 | 253 |
| 20 DMMP, MED RH | 1 | 627 | 24 | 0 |
| 21 AMMONIA, MED RH | 50 | 0 | 244 | 59 |
| 22 AMMONIA/GD, MED RH | 50/.5 | 86 | 330 | 132 |
| 23 DCP, MED RH | 35 | 0 | 66 | 300 |
| 24 DMMP, MED RH | 1 | 843 | 24 | 0 |
| 25 MES, DRY | 20 | 151 | 281 | 280 |
| 26 MES, DRY | 20 | 372 | 507 | 505 |
| 27 MES, DRY | 20 | 496 | 606 | 605 |

TABLE 8

Prediction Set of Data Collected in Preconcentrator Sampling Mode in System Check Testing at Calspan

| | CONC | FREQUENCY SHIFTS (Hz) | | |
|---|---|---|---|---|
| TEST VAPOR | mg/m3 | FPOL | ECEL | PECH |
| 1 DMMP, MED RH | .1 | 1539 | 105 | 262 |
| 2 DMMP, MED RH | .1 | 1575 | 84 | 265 |
| 3 DMMP, MED RH | .1 | 1545 | 94 | 279 |
| 4 DMMP, MED RH | .1 | 1616 | 100 | 270 |
| 5 DMMP, MED RH | .1 | 1532 | 103 | 270 |
| 6 DMMP, MED RH | .1 | 1467 | 98 | 260 |
| 7 DMMP, MED RH | .1 | 1533 | 106 | 267 |
| 8 DMMP, MED RH | .1 | 1587 | 104 | 290 |
| 9 DMMP, MED RH | .1 | 1498 | 98 | 265 |
| 10 DMMP, MED RH | 1 | 15515 | 533 | 2500 |
| 11 DMMP, MED RH | 1 | 15637 | 538 | 2457 |
| 12 DMMP, MED RH | 1 | 15589 | 507 | 2487 |
| 13 DMMP, MED RH | 1 | 15668 | 537 | 2463 |
| 14 DMMP, MED RH | 1 | 15601 | 507 | 2510 |
| 15 DMMP, MED RH | 1 | 15543 | 573 | 2496 |
| 16 DMMP, MED RH | 1 | 15595 | 532 | 2508 |
| 17 DMMP, MED RH | 1 | 15707 | 542 | 2532 |
| 18 DMMP, MED RH | 1 | 15822 | 540 | 2527 |
| 19 DMMP, MED RH | 1 | 15829 | 530 | 2496 |
| 20 DCP, MED RH | 3 | 527 | 404 | 2035 |
| 21 DCP, MED RH | 3 | 514 | 418 | 2093 |
| 22 DCP, MED RH | 3 | 520 | 425 | 2081 |
| 23 DCP, MED RH | 3 | 531 | 422 | 2129 |
| 24 DCP, MED RH | 3 | 523 | 409 | 2111 |
| 25 HD, MED RH | .05 | 0 | 68 | 157 |
| 26 HD, MED RH | .05 | 0 | 168 | |
| 27 HD, MED RH | .05 | 60 | 0 | 166 |

TABLE 8-continued

Prediction Set of Data Collected in Preconcentrator Sampling Mode in System Check Testing at Calspan

| | CONC | FREQUENCY SHIFTS (Hz) | | |
|---|---|---|---|---|
| TEST VAPOR | mg/m3 | FPOL | ECEL | PECH |
| 28 HD, MED RH | .05 | 64 | 0 | 151 |
| 29 HD, MED RH | .05 | 0 | 0 | 178 |
| 30 GD, MED RH | .5 | 3755 | 154 | 494 |
| 31 GD, MED RH | .5 | 3630 | 121 | 484 |
| 32 GD, MED RH | .5 | 3813 | 130 | 479 |
| 33 GD, MED RH | .5 | 3829 | 123 | 483 |
| 34 GD, MED RH | .5 | 3763 | 121 | 477 |
| 35 GD, MED RH | .5 | 3796 | 129 | 480 |
| 36 GD, MED RH | .5 | 3856 | 134 | 499 |
| 37 HD, MED RH | .05 | 54 | 0 | 159 |
| 38 HD, MED RH | .05 | 0 | 0 | 165 |
| 39 HD, MED RH | .05 | 56 | 0 | 149 |
| 40 HD, MED RH | .05 | 0 | 0 | 169 |
| 41 HD, MED RH | .05 | 51 | 62 | 176 |
| 42 DMMP, MED RH | .1 | 1966 | 103 | 165 |
| 43 DMMP, MED RH | .1 | 1916 | 86 | 163 |
| 44 DMMP, MED RH | .1 | 1900 | 108 | 141 |
| 45 DMMP, MED RH | .1 | 1871 | 97 | 175 |
| 46 DMMP, MED RH | .1 | 1904 | 99 | 166 |
| 47 DMMP, MED RH | .1 | 1962 | 110 | 168 |
| 48 DMMP, MED RH | .1 | 1913 | 102 | 166 |
| 49 DMMP, MED RH | .1 | 1896 | 105 | 165 |
| 50 DCP, MED RH | 3 | 578 | 442 | 2196 |
| 51 DCP, MED RH | 3 | 518 | 417 | 2235 |
| 52 DCP, MED RH | 3 | 499 | 426 | 2232 |
| 53 DCP, MED RH | 3 | 573 | 453 | 2300 |
| 54 DCP, MED RH | 35 | 11169 | 2735 | 71991 |
| 55 DCP, MED RH | 35 | 11487 | 2581 | 73718 |
| 56 DCP, MED RH | 35 | 11587 | 2486 | 73453 |
| 57 DCP, MED RH | 35 | 11512 | 2336 | 74085 |
| 58 DCP, MED RH | 35 | 11321 | 2212 | 74396 |
| 59 HD, MED RH | .5 | 310 | 331 | 2267 |
| 60 HD, MED RH | .5 | 260 | 315 | 2275 |
| 61 HD, MED RH | .5 | 268 | 349 | 2249 |
| 62 HD, MED RH | .5 | 303 | 310 | 2288 |
| 63 HD, MED RH | .5 | 292 | 333 | 2283 |
| 64 GD, MED RH | .05 | 350 | 54 | 130 |
| 65 GD, MED RH | .05 | 352 | 0 | 131 |
| 66 GD, MED RH | .05 | 355 | 155 | 121 |
| 67 GD, MED RH | .05 | 348 | 53 | 143 |
| 68 GD, MED RH | .05 | 360 | 77 | 136 |
| 69 GD, MED RH | .05 | 332 | 52 | 121 |
| 70 GD, MED RH | .05 | 331 | 0 | 144 |
| 71 GD, MED RH | .05 | 296 | 51 | 131 |
| 72 HD, MED RH | .5 | 322 | 307 | 2240 |
| 73 HD, MED RH | .5 | 299 | 307 | 2242 |
| 74 HD, MED RH | .5 | 330 | 300 | 2253 |
| 75 HD, MED RH | .5 | 313 | 333 | 2262 |
| 76 HD, MED RH | .5 | 305 | 332 | 2272 |
| 77 DCP, MED RH | 35 | 11442 | 1992 | 75830 |
| 78 DCP, MED RH | 35 | 11501 | 1877 | 76263 |
| 79 DCP, MED RH | 35 | 11396 | 1657 | 76459 |
| 80 DCP, MED RH | 35 | 11526 | 1692 | 77141 |
| 81 DCP, MED RH | 35 | 11620 | 1781 | 76865 |
| 82 VX, MED RH | .05 | 11358 | 446 | 1114 |
| 83 VX, MED RH | .05 | 11578 | 320 | 1135 |
| 84 VX, MED RH | .05 | 11656 | 360 | 1151 |
| 85 VX, MED RH | .05 | 11642 | 360 | 1132 |
| 86 VX, MED RH | .0005 | 65 | 0 | 69 |
| 87 VX, MED RH | .0005 | 60 | 0 | 58 |
| 88 VX, MED RH | .0005 | 84 | 0 | 61 |
| 89 VX, MED RH | .0005 | 63 | 0 | 59 |
| 90 VX, MED RH | .5 | 26446 | 496 | 2688 |
| 91 VX, MED RH | .5 | 26502 | 433 | 2727 |
| 92 VX, MED RH | .5 | 26411 | 531 | 18077 |
| 93 VX, MED RH | .5 | 25813 | 649 | 2722 |
| 94 VX, MED RH | .5 | 25650 | 697 | 2742 |
| 95 BLEACH, LOW RH | ? | 165 | 0 | 0 |
| 96 BLEACH, LOW RH | ? | 119 | 0 | 261 |
| 97 BLEACH, LOW RH | ? | 134 | 153 | 256 |
| 98 BLEACH, LOW RH | ? | 69 | 0 | 0 |

TABLE 8-continued

Prediction Set of Data Collected in Preconcentrator Sampling Mode in System Check Testing at Calspan

| TEST VAPOR | CONC mg/m3 | FREQUENCY SHIFTS (Hz) | | |
|---|---|---|---|---|
| | | FPOL | ECEL | PECH |
| 99 BLEACH, LOW RH | ? | 125 | 152 | 271 |
| 100 BLEACH/HD, MED, RH | ?/2.0 | 510 | 664 | 4672 |
| 101 BLEACH/HD, MED, RH | ?/2.0 | 511 | 0 | 4630 |
| 102 BLEACH/HD, MED, RH | ?/2.0 | 616 | 0 | 4574 |
| 103 BLEACH/HD, MED, RH | ?/2.0 | 556 | 0 | 4575 |
| 104 BLEACH/HD, MED, RH | ?/2.0 | 515 | 817 | 4615 |
| 105 BLEACH/GD, MED, RH | ?/.5 | 2821 | 138 | 390 |
| 106 BLEACH/GD, MED, RH | ?/.5 | 2811 | 125 | 389 |
| 107 BLEACH/GD, MED, RH | ?/.5 | 2TT7 | 137 | 400 |
| 108 BLEACH/GD, MED, RH | ?/.5 | 2725 | 123 | 400 |
| 109 BLEACH/GD, MED, RH | ?/.5 | 2690 | 0 | 399 |
| 110 BLEACH/HD, MED, RH | ?/2.0 | 494 | 0 | 4780 |
| 111 BLEACH/HD, MED, RH | ?/2.0 | 793 | 869 | 4658 |
| 112 BLEACH/HD, MED, RH | ?/2.0 | 628 | 868 | 4725 |
| 113 BLEACH/HD, MED, RH | ?/2.0 | 619 | 865 | 4715 |
| 114 BLEACH/GD, MED, RH | ?/.5 | 2633 | 114 | 391 |
| 115 BLEACH/GD, MED, RH | ?/.5 | 2521 | 107 | 394 |
| 116 BLEACH/GD, MED, RH | ?/.5 | 2568 | 102 | 393 |
| 117 BLEACH/GD, MED, RH | ?/.5 | 2511 | 128 | 403 |
| 118 BLEACH/GD, MED, RH | ?/.5 | 2510 | 111 | 408 |
| 119 BLEACH, LOW RH | ? | 70 | 0 | 286 |
| 120 BLEACH, LOW RH | ? | 138 | 107 | 296 |
| 121 BLEACH, LOW RH | ? | 52 | 155 | 308 |
| 122 BLEACH, LOW RH | ? | 91 | 0 | 320 |
| 123 BLEACH, LOW RH | ? | 104 | 0 | 307 |
| 124 VX, MED RH | .5 | 25916 | 789 | 2744 |
| 125 VX, MED RH | .5 | 25625 | 808 | 2762 |
| 126 VX, MED RH | .5 | 25441 | 881 | 2753 |
| 127 VX, MED RH | .5 | 25331 | 885 | 2779 |
| 128 VX, MED RH | .05 | 11696 | 449 | 1116 |
| 129 VX, MED RH | .05 | 11663 | 379 | 1133 |
| 130 VX, MED RH | .05 | 11593 | 505 | 1129 |
| 131 VX, MED RH | .05 | 11601 | 370 | 1115 |
| 132 VX, MED RH | .05 | 11639 | 455 | 1122 |
| 133 VX, MED RH | .0005 | 68 | 0 | 0 |
| 134 VX, MED RH | .0005 | 107 | 0 | 0 |
| 135 VX, MED RH | .0005 | 79 | 0 | 0 |
| 136 VX, MED RH | .0005 | 72 | 0 | 0 |
| 137 HD, MED RH | 2 | 741 | 624 | 7438 |
| 138 HD, MED RH | 2 | 739 | 623 | 7398 |
| 139 HD, MED RH | 2 | 738 | 637 | 7404 |
| 140 HD, MED RH | 2 | 754 | 710 | 7392 |
| 141 HD, MED RH | 2 | 745 | 706 | 7415 |
| 142 HD, MED RH | 2 | 791 | 642 | 7579 |
| 143 HD, MED RH | 2 | 803 | 635 | 7516 |
| 144 HD, MED RH | 2 | 758 | 652 | 7443 |
| 145 HD, MED RH | 2 | 753 | 674 | 7508 |
| 146 HD, MED RH | 2 | 751 | 669 | 7513 |
| 147 AMMONIA/GD, MED, RH | 50/0.5 | 7772 | 218 | 427 |
| 148 AMMONIA/GD, MED, RH | 50/0.5 | 7831 | 215 | 423 |
| 149 AMMONIA/GD, MED, RH | 50/0.5 | 7713 | 214 | 421 |
| 150 AMMONIA/GD, MED, RH | 50/0.5 | 7663 | 224 | 417 |
| 151 AMMONIA/GD, MED, RH | 50/0.5 | 7685 | 226 | 419 |
| 152 AMMONIA/GD, MED, RH | 50/0.5 | 7608 | 227 | 426 |
| 153 AMMONIA/GD, MED, RH | 50/0.5 | 7593 | 223 | 424 |
| 154 AMMONIA/GD, MED, RH | 50/0.5 | 7512 | 228 | 428 |
| 155 AMMONIA/GD, MED, RH | 50/0.5 | 7401 | 224 | 370 |
| 156 AMMONIA/GD, MED, RH | 50/0.5 | 7431 | 212 | 403 |
| 157 AMMONIA/HD, MED, RH | 50/2 | 732 | 596 | 2730 |
| 158 AMMONIA/HD, MED, RH | 50/2 | 781 | 591 | 2694 |
| 159 AMMONIA/HD, MED, RH | 50/2 | 778 | 614 | 2702 |
| 160 AMMONIA/HD, MED, RH | 50/2 | 827 | 635 | 2712 |
| 161 AMMONIA/HD, MED, RH | 50/2 | 809 | 622 | 2711 |
| 162 AMMONIA/HD, MED, RH | 50/2 | 816 | 639 | 2720 |
| 163 AMMONIA/HD, MED, RH | 50/2 | 814 | 653 | 2695 |
| 164 AMMONIA/HD, MED, RH | 50/2 | 839 | 674 | 2672 |
| 165 AMMONIA/HD, MED, RH | 50/2 | 810 | 656 | 2667 |
| 166 BLEACH, MED RH | ? | 136 | 467 | 275 |
| 167 BLEACH, MED RH | ? | 120 | 487 | 282 |
| 168 BLEACH, MED RH | ? | 126 | 562 | 331 |
| 169 BLEACH, MED RH | ? | 102 | 272 | 359 |
| 170 BLEACH, MED RH | ? | 124 | 509 | 343 |
| 171 HD/SO2, MED RH | 2/50 | 413 | 620 | 5573 |
| 172 HD/SO2, MED RH | 2/50 | 398 | 618 | 5440 |
| 173 HD/SO2, MED RH | 2/50 | 399 | 621 | 5402 |
| 174 HD/SO2, MED RH | 2/50 | 413 | 619 | 5401 |
| 175 HD/SO2, MED RH | 2/50 | 422 | 623 | 5458 |
| 176 HD/SO2, MED RH | 2/50 | 449 | 648 | 5662 |
| 177 HD/SO2, MED RH | 2/50 | 426 | 636 | 5498 |
| 178 HD/SO2, MED RH | 2/50 | 451 | 630 | 5499 |
| 179 HD/SO2, MED RH | 2/50 | 483 | 649 | 5507 |
| 180 GD/SO2, MED RH | 0.5/50 | 1625 | 94 | 0 |
| 181 GD/SO2, MED RH | 0.5/50 | 1620 | 84 | 0 |
| 182 GD/SO2, MED RH | 0.5/50 | 1651 | 105 | 328 |
| 183 GD/SO2, MED RH | 0.5/50 | 1576 | 84 | 329 |
| 184 GD/SO2, MED RH | 0.5/50 | 1585 | 92 | 0 |
| 185 GD/SO2, MED RH | 0.5/50 | 1551 | Be | 326 |
| 186 GD/SO2, MED RH | 0.5/50 | 1496 | 86 | 333 |
| 187 GD/SO2, MED RH | 0.5/50 | 1583 | 88 | 344 |
| 188 GD/SO2, MED RH | 0.5/50 | 1563 | 96 | 341 |
| 189 GD/SO2, MED RH | 0.5/50 | 1549 | 100 | 339 |
| 190 VX, MED RH | .05 | 3059 | 286 | 463 |
| 191 VX, MED RH | .05 | 2997 | 0 | 478 |
| 192 VX, MED RH | .05 | 2973 | 258 | 485 |
| 193 VX, MED RH | .05 | 2956 | 268 | 473 |
| 194 VX, MED RH | .05 | 2982 | 270 | 476 |
| 195 VX, MED RH | .05 | 3019 | 253 | 0 |
| 196 VX, MED RH | .05 | 2999 | 253 | 0 |
| 197 VX, MED RH | .05 | 3107 | 250 | 469 |
| 198 VX, MED RH | .5 | 15678 | 650 | 1540 |
| 199 VX, MED RH | .5 | 15771 | 667 | 1507 |
| 200 VX, MED RH | .5 | 16226 | 653 | 1548 |
| 201 VX, MED RH | .5 | 15954 | 653 | 1565 |
| 202 VX, MED RH | .5 | 16335 | 660 | 1520 |

TABLE 8-continued

Prediction Set of Data Collected in Preconcentrator Sampling Mode in System Check Testing at Calspan

| TEST VAPOR | CONC mg/m3 | FPOL | ECEL | PECH |
|---|---|---|---|---|
| 203 VX, MED RH | .5 | 16363 | 647 | 1490 |
| 204 VX, MED RH | .5 | 16311 | 617 | 1531 |
| 205 VX, MED RH | .5 | 16286 | 606 | 1481 |
| 206 VX, MED RH | .5 | 16521 | 561 | 1507 |
| 207 VX, MED RH | .5 | 16500 | 522 | 1499 |
| 208 GD/HD, MED RH | 0.5/2 | 2442 | 761 | 9187 |
| 209 GD/HD, MED RH | 0.5/2 | 2426 | 814 | 9354 |
| 210 GD/HD, MED RH | 0.5/2 | 2413 | 819 | 9501 |
| 211 GD/HD, MED RH | 0.5/2 | 2471 | 835 | 9493 |
| 212 GD/HD, MED RH | 0.5/2 | 2476 | 952 | 9528 |
| 213 GD/HD, MED RH | 0.5/2 | 2524 | 822 | 9632 |
| 214 GD/HD, MED RH | 0.5/2 | 2422 | 198 | 9491 |
| 215 GD/HD, MED RH | 0.5/2 | 2436 | 807 | 9475 |
| 216 GD/HD, MED RH | 0.5/2 | 2422 | 865 | 9527 |
| 217 GD/HD, MED RH | 0.5/2 | 2396 | 841 | 9601 |
| 218 DMMP, MED RH | .1 | 1061 | 67 | 274 |
| 219 DMMP, MED RH | .1 | 1067 | 71 | 273 |
| 220 DMMP, MED RH | .1 | 1045 | 60 | 253 |
| 221 DMMP, MED RH | .1 | 1067 | 70 | 270 |
| 222 DMMP, MED RH | .1 | 1101 | 77 | 276 |
| 223 DMMP, MED RH | .1 | 1062 | 58 | 273 |
| 224 DMMP, MED RH | .1 | 1085 | 75 | 256 |
| 225 DMMP, MED RH | .1 | 1090 | 76 | 270 |
| 226 DMMP, MED RH | .1 | 1031 | 68 | 270 |

TABLE 9

Prediction Set of Data Collected in Preconcentrator Sampling Mode at NRL

| TEST VAPOR | CONC mg/m3 | FPOL | ECEL | PECH |
|---|---|---|---|---|
| 1 MES, MED RH | 10 | 53 | 0 | 0 |
| 2 MES, MED RH | 10 | 50 | 0 | 0 |
| 3 MES, MED RH | 10 | 52 | 0 | 0 |
| 4 MES, MED RH | .16 | 87 | 67 | 67 |
| 5 MES, MED RH | .16 | 71 | 74 | 75 |
| 6 MES, MED RH | .16 | 76 | 0 | 0 |
| 7 MES, MED RH | .16 | 71 | 0 | 0 |
| 8 MES, DRY | 20 | 0 | 460 | 0 |
| 9 MES, DRY | 20 | 0 | 496 | 0 |
| 10 MES, DRY | 20 | 0 | 547 | 0 |
| 11 MES, DRY | 20 | 0 | 514 | 0 |
| 12 MES, DRY | 20 | 0 | 534 | 0 |
| 13 MES, DRY | 20 | 0 | 1069 | 0 |
| 14 MES, DRY | 20 | 0 | 1068 | 0 |
| 15 MES, DRY | 20 | 0 | 1102 | 0 |
| 16 MES, DRY | 20 | 0 | 1108 | 0 |
| 17 MES, DRY | 20 | 0 | 1117 | 0 |
| 18 DEM, DRY | .11 | 109 | 0 | 320 |
| 19 DEM, DRY | .11 | 128 | 104 | 313 |
| 20 DEM, DRY | .11 | 132 | 111 | 331 |
| 21 DEM, DRY | .11 | 126 | 0 | 325 |
| 22 DEM, DRY | .11 | 126 | 0 | 323 |
| 23 DEM, DRY | .11 | 135 | 0 | 337 |
| 24 DEM, DRY | .11 | 0 | 0 | 324 |
| 25 DEM, DRY | .11 | 127 | 83 | 316 |
| 26 DEM, DRY | .11 | 135 | 0 | 328 |
| 27 DEM, DRY | .11 | 142 | 104 | 336 |
| 28 MES, HIGH RH | .16 | 76 | 59 | 61 |
| 29 MES, HIGH RH | .16 | 64 | 0 | 0 |
| 30 MES, HIGH RH | .16 | 80 | 55 | 55 |
| 31 MES, HIGH RH | .16 | 54 | 0 | 0 |
| 32 MES, HIGH RH | .16 | 65 | 52 | 52 |
| 33 MES, HIGH RH | .16 | 75 | 63 | 62 |
| 34 MES, HIGH RH | .16 | 67 | 51 | 52 |
| 35 DCP, MED RH | 42 | 15338 | 35308 | 49058 |
| 36 DCP, MED RH | 42 | 15010 | 33572 | 48598 |
| 37 DCP, MED RH | 42 | 15272 | 34262 | 51318 |
| 38 DCP, MED RH | 42 | 15403 | 34218 | 51917 |
| 39 DCP, MED RH | 42 | 15290 | 33807 | 51735 |
| 40 DCP, MED RH | 42 | 15105 | 36705 | 46116 |
| 41 DCP, MED RH | 42 | 15283 | 36266 | 48897 |
| 42 DCP, MED RH | 42 | 15318 | 35421 | 50009 |
| 43 DCP, MED RH | 42 | 15557 | 35678 | 52112 |
| 44 DCP, MED RH | 42 | 15114 | 34511 | 50499 |
| 45 DEM, MED RH | .11 | 188 | 64 | 331 |
| 46 DEM, MED RH | .11 | 226 | 68 | 330 |
| 47 DEM, MED RH | .11 | 235 | 131 | 330 |
| 48 DEM, MED RH | .11 | 217 | 65 | 316 |
| 49 DEM, MED RH | .11 | 230 | 118 | 322 |
| 50 DEM, MED RH | .11 | 231 | 121 | 330 |
| 51 DEM, MED RH | .11 | 230 | 69 | 333 |
| 52 DEM, MED RH | .11 | 247 | 131 | 336 |
| 53 DEM, MED RH | .11 | 241 | 125 | 342 |
| 54 DEM, MED RH | .11 | 228 | 69 | 323 |
| 55 DEM, MED RH | .11 | 242 | 126 | 328 |
| 56 DEM, MED RH | .11 | 224 | 67 | 321 |
| 57 DEM, MED RH | .11 | 227 | 109 | 323 |
| 58 DEM, MED RH | .11 | 231 | 66 | 326 |
| 59 DEM, MED RH | .11 | 237 | 0 | 324 |
| 60 DEM, MED RH | 1.1 | 1858 | 631 | 1932 |
| 61 DEM, MED RH | 1.1 | 1868 | 629 | 1905 |
| 62 DEM, MED RH | 1.1 | 1892 | 640 | 1937 |
| 63 DEM, MED RH | 1.1 | 1915 | 641 | 1955 |
| 64 DEM, MED RH | 1.1 | 1915 | 643 | 1944 |
| 65 DEM, MED RH | 1.1 | 1945 | 658 | 2000 |
| 66 DEM, MED RH | 1.1 | 1971 | 670 | 1998 |
| 67 DEM, MED RH | 1.1 | 2016 | 682 | 2047 |
| 68 DEM, MED RH | 1.1 | 2035 | 704 | 2079 |

TABLE 10

Summary of Results from Algorithm and System Check Testing

| Vapor | Concentration(s) mg/m³ | CORRECT CLASSIFICATION[a] | Comments |
|---|---|---|---|
| | | Nerve Agents and Simulants, Including Mixtures | |
| GD | 0.01, 0.05, 0.5, 5 | YES | 0.0005 mg/m³ also tested but not detected. Detect 0.01 mg/m³ in two minutes. 5 mg/m³ detected and identified in 10–20 seconds. By extrapolatoin, 1 mg/m³ could be detected in 20 seconds. |
| VX | 0.01, .05, 0.5 | YES | 0.0005 mg/m³ also tested, detected and correctly classified in two minutes, but the signals were small. |

TABLE 10-continued

Summary of Results from Algorithm and System Check Testing

| Vapor | Concentration(s) mg/m³ | | Comments |
|---|---|---|---|
| DMMP | 0.1, 1, 10 | YES | 0.01 mg/m³ detected in two minutes. 0.05 mg/m³ sometimes detected in 30 seconds. 0.5 mg/m³ detected and identified in 20–30 seconds. 0.1 mg/m³ detected in 2 minutes. 1 mg/m³ detected in ca. 10 seconds. |
| GD/JP-4 | 0.5/50 | YES | Detected and identified in 2 minutes. |
| GD/gasoline | 0.5/50 | YES | Detected and identified in 2 minutes. |
| GD/diesel | 0.5/50 | YES | Detected and identified in 2 minutes. |
| GD/dichloroethane | 0.5/50 | YES | Detected and identified in 2 minutes. |
| GD/isopropanol | 0.5/50 | YES | Detected and identified in 2 minutes. |
| GD/ammonia | 0.5/50 | YES | Detected and identified in 2 minutes. |
| GD/sulfur dioxide | 0.5/50 | YES | Detected and identified in 2 minutes. |
| GD/bleach | 0.5/50 | YES | Detected and identified in 2 minutes. |
| Blister Agent, Including Mixtures | | | |
| HD | 0.05, 0.5, 2, 10 | YES | Detection with correct classification at 0.5 mg/m³ and above in 2 minutes. Detected at 0.05 mg/m³ in two minutes and usually correctly classified. Detection with correct classification at 10 mg/m³ and sometimes 2 mg/m³ within 10 to 20 seconds. |
| HD/JP-4 | 2.0/50 | YES | Detected and identified in 2 minutes. |
| HD/gasoline | 2.0/50 | YES | Detected and identified in 2 minutes. |
| HD/diesel | 2.0/50 | YES | Detected and identified in 2 minutes. |
| HD/dichloroethane | 2.0/50 | YES | Detected and identified in 2 minutes. |
| HD/isopropanol | 2.0/50 | YES | Detected and identified in 2 minutes. |
| HD/ammonia | 2.0/50 | YES | Detected and identified in 2 minutes. Also detected and correctly classified in direct sampling mode at medium humidity. |
| HD/sulfur dioxide | 2.0/50 | YES | Detected and identified in 2 minutes. |
| HD/bleach | 2.0/50 | YES | Detected and identified in 2 minutes. |

| Vapor | Concentration(s) mg/m³ | FALSE ALARM[b] | Comments |
|---|---|---|---|
| Potential Background Vapors Specified by the Air Force: Organic Vapors | | | |
| dichloroethane | 50 | NO | Not detected in direct sampling Detected at short desorption time in two minute preconcentrator mode: algorithms successfully discriminate against it. |
| isopropanol | 50 | NO | Not detected in direct sampling mode. Barely detected at short desorption time in two minute preconcentrator mode: algorithms successfully discriminate against it. |
| JP-4/JP-5 vapors | 50 | NO | Not detected in direct sampling mode. Barely detected at short desorption time in two minute preconcentrator mode: algorithms successfully discriminate against it. |
| gasoline vapors | 50 | NO | Not detected in direct sampling mode. Detected at short desorption time in two minute preconcentrator mode: algorithms successfully discriminate against it. |
| diesel vapors | 50 | NO (see comment) | Normally not detected in direct sampling mode. In one spurious test signals were observed that cause a blister false alarm if one tries to detect blister faster than the required two minutes. Detected in two minute preconcentrator mode, but pattern is distinct from GD so it can be successfully discriminated against, and desorption is faster than HD and it can be successfully discriminated against. |
| Potential Background Aerosols Specified by the Air Force | | | |
| gasoline exhaust | .01 | NO | For all the aerosols (exhausts and smoke), the main effect was a change in humidity as evidenced by the PEI response. The other 3 sensors did register signals, however, the algorithms successfully discriminate against them. |
| diesel exhaust | .2 | NO | See above. |
| jet exhaust | N/A | NO | See above. |
| cigarette smoke | 5 | NO | See above. |
| Potential Background Vapors Specified by the Air Force: Inorganic Vapors | | | |
| ammonia | 50 | NO(see comment) | Unrealistically high test concentrations (TLV is only 18 mg/m³ -see text). At test concentration barely detected at medium humidity in direct mode, and at limit of detection in two minute preconcentrator mode. At 5 mg/m³, no signals would be expected, and hence no false alarm could occur. At the high test concentrations the weak reponses seen were correctly discriminated against by nerve agent algorithms and the blister agent two minute algorithm. Only in the case of |

TABLE 10-continued

Summary of Results from Algorithm and System Check Testing

|  |  |  |  |
|---|---|---|---|
|  |  |  | direct sampling did blister agent algorithms misclassify the ammonia responses, and it is not necessary to perform blister agent classification in direct mode to meet the Air Force requirements |
| sulfur dioxide | 50 | NO | Not detected in either direct mode or two minute preconcentrator mode. |
| bleach | ? | SOMETIMES | Test results highly variable. Sometimes caused misclassification in both nerve and blister agent detection. |

Additional Notes
1. The GD/HD mixture was correctly classified as containing HD, but the GD in the mixture was not correctly recognized by the nerve agent algorithm.
2. HD exposures can sometimes give a false alarm for nerve agent. They are correctly recognized as containing blister. Therefore, in these cases, an HD exposure can cause both a nerve and blister alarm.
3. DCP is not an effective quantitative simulant for HD, but it could be used as a qualitative HD simulant in two minute preconcentrator sampling mode if the peak window is widened - see text
4. MES and DEM are not effective simulants for either nerve or blister agents.
5. Isooctane and toluene were tested at NRL. Toluene can be detected at 500 mg/m$^3$ in direct sampling, but is barely detectable sometimes at 50 mg/m$^3$. With the two minute preconcentrator, toluene at 50 mg/m$^3$ can be detected but the desorption time is much shorter than those of agents: algorithms successfully discriminate against it. Isooctane is not detected in either mode at 50 or even 120 mg/m$^3$. Therefore neither of these vapors cause false alarms.
6. The mixture of ammnonia and GD was incorrectly classified as a blister agent in direct sampling mode. But it is not necessary to test for blister agent in direct sampling mode.
[a]Classification results at detectable levels.
[b]No false alarm because it was not detected at all, or if detected, the algorithms correctly discriminated against it.

What is claimed is:

1. A method of identifying an unknown vapor as either belonging to a class or not, wherein the class comprises known vapors of interest, said method comprising the steps of:

introducing a sample of an unknown vapor into at least one sensor coated with a vapor-sensitive coating, generating a weight vector corresponding to a N-space representation of the class;

generating a N-space representation of the unknown vapor and generating an unknown pattern vector based thereon; and calculating the dot product of said unknown pattern vector and the weight vector to determine whether the unknown vapor is within said class, wherein the dot product producing a positive number is a member of the class in question while a negative number is not.

2. The method recited in claim 1, wherein said step of generating a weight vector comprises the steps of:

selecting a training set comprising a subset of the known vapors of interest and background vapors;

generating an N-space representation of said training set so as to create an associated weight vector; and storing said weight vector in memory for use in calculating said dot product.

3. The method recited in claim 2, wherein said step of generating an N-space representation of said training set further comprises the steps of:

generating vapor response data from a sensor array comprising at least two sensors;

interpreting a pattern of responses as a point in an N-dimensional feature space having N axes and defining a pattern vector extending from the origin of said axes to said point, where N is defined by the number of sensors in said sensor array; and using a supervised learning technique to generate a discriminant function which defines a weight vector, a first cluster of points corresponding to the known vapors, and a second cluster of points corresponding to the background vapors.

4. The method recited in claim 3, wherein said step of using supervised learning techniques to generate a discriminant function further comprises the step of:

using a Bayes linear equation to iteratively generate said weight vector.

5. The method recited in claim 4 further comprising the step of comparing results of said dot product with a vector associated with each known pattern result to determine if a correction factor is required; and iteratively repeating the last step until all results agree with known results.

6. The method recited in claim 3, wherein said step of using a supervised learning technique to generate a discriminant further comprises the step of:

using a nonparametric equation selected from the group consisting of linear learning machines, adaptive least squares classifiers and combinations thereof, to iteratively generate said weight vector.

7. The method recited in claim 3, wherein said step of using a supervised learning technique to generate a discriminant further comprises the step of:

using a parametric equation to iteratively generate said weight vector; and passing said weight vector to at least one further supervised learning technique to increase the accuracy of said weight vector.

8. The method recited in claim 1, wherein said step of generating a N-space representation of the unknown vapor comprises the steps of:

generating unknown vapor response data from a sensor array comprising at least two sensors; and interpreting a pattern of said unknown response as a point in an N-dimensional feature space having N axes and defining an unknown pattern vector extending from the origin of said axes to said point, where N is defined by the number of sensors in said sensor array.

9. A smart sensor system for determining whether an unknown vapor is within a known class of vapors, said system comprising:

a sampling means for generating vapor samples;

an array of sensors for generating vapor response data from said vapor samples;

means for interpreting said response data as points in an

N-dimensional feature space having N axes and defining unknown pattern vectors, each vector being associated with one of said points and extending from the origin of said axes to said point, where N is defined by the number of sensors in said sensor array; and means for calculating the dot product of said unknown pattern vector and a stored weighing vector associated with a N-space representation of the known class, and to determine if said vapor is within said class, said weight vector being defined by a discriminant function generated by a supervised learning technique.

10. The system recited in claim 9 wherein each of said sensors comprises a transducer having vapor a sensitive coating disposed thereon for providing sorbing of said vapors to thereby increase the mass and decrease the modulus of said coating.

11. The system recited in claim 10 wherein said vapor sensitive coating is selected from a group consisting of poly(ethylenimine), fluoropolyol, ethyl cellulose, poly(epichlorohydrin), poly(isobutylene), poly(ethylene maleate), poly(ethylene phthalate), and combinations thereof.

12. The system recited in claim 9 further comprising a temperature control means for maintaining said sensors at a predetermined temperature.

* * * * *